(12) United States Patent
Yum et al.

(10) Patent No.: US 10,751,393 B2
(45) Date of Patent: Aug. 25, 2020

(54) BACILLUS AMYLOLIQUEFACIENS GF423 STRAIN, AND COMPOSITION FOR PROVIDING ANTIOXIDANT AND ANTI-INFLAMMATORY ACTIVITIES OR PREVENTING OR TREATING HYPERLIPIDEMIA, INCLUDING POLYPEPTIDE PRODUCED BY THE SAME

(71) Applicant: GENOFOCUS, INC., Daejeon (KR)

(72) Inventors: Do Young Yum, Daejeon (KR); Jeong Hyun Kim, Seongnam-si (KR); Jae Gu Pan, Sejong (KR); Eui Joong Kim, Daejeon (KR); Taek Ho Yang, Daejeon (KR); Ji Eun Kang, Icheon-si (KR); Soo Young Park, Daejeon (KR); Hyun Do Kim, Gwangju (KR)

(73) Assignee: GENOFOCUS INC., Yuseong-Gu, Daejeon (KR)

( * ) Notice: Subject to any disclaimer, the term of this patent is extended or adjusted under 35 U.S.C. 154(b) by 0 days.

(21) Appl. No.: 16/482,982

(22) PCT Filed: Mar. 7, 2018

(86) PCT No.: PCT/KR2018/002677
§ 371 (c)(1),
(2) Date: Aug. 1, 2019

(87) PCT Pub. No.: WO2018/164468
PCT Pub. Date: Sep. 13, 2018

(65) Prior Publication Data
US 2019/0343928 A1    Nov. 14, 2019

(30) Foreign Application Priority Data

Mar. 9, 2017 (KR) .................. 10-2017-0030300
Mar. 9, 2017 (KR) .................. 10-2017-0030301
Sep. 12, 2017 (KR) .................. 10-2017-0116305

(51) Int. Cl.
| | | |
|---|---|---|
| *A61K 38/44* | (2006.01) | |
| *A23K 10/18* | (2016.01) | |
| *C12N 1/20* | (2006.01) | |
| *C12R 1/07* | (2006.01) | |
| *A23K 20/142* | (2016.01) | |
| *A23K 20/195* | (2016.01) | |
| *A23L 33/18* | (2016.01) | |
| *A61Q 19/00* | (2006.01) | |
| *A61K 8/64* | (2006.01) | |

(52) U.S. Cl.
CPC .......... *A61K 38/446* (2013.01); *A23K 10/18* (2016.05); *A23K 20/142* (2016.05); *A23K 20/195* (2016.05); *A23L 33/18* (2016.08); *A61K 8/64* (2013.01); *A61Q 19/008* (2013.01); *C12N 1/20* (2013.01); *C12R 1/07* (2013.01); *C12Y 115/01001* (2013.01)

(58) Field of Classification Search
CPC .......... A61K 38/446; A61K 8/64; C12R 1/07; A23K 20/195; A23K 20/142; A23K 10/18; A23L 33/18; C12N 1/20; A61Q 19/008; C12Y 115/01001
See application file for complete search history.

(56) References Cited

U.S. PATENT DOCUMENTS

| | | | | |
|---|---|---|---|---|
| 5,667,999 A | * | 9/1997 | Koh .................. | A61K 35/742 435/189 |
| 2004/0234560 A1 | * | 11/2004 | Kimura ............... | A61K 8/97 424/401 |
| 2008/0003641 A1 | * | 1/2008 | Hsieh ................. | C12N 9/0089 435/69.1 |

FOREIGN PATENT DOCUMENTS

| | | |
|---|---|---|
| KR | 10-2012-0111091 | 10/2012 |
| KR | 10-1762199 | 7/2017 |
| KR | 10-1814035 | 1/2018 |

OTHER PUBLICATIONS

He et al., GenBank accession No. AFJ62706, Jan. 30, 2014.*
Yang et al., GenBank AIW34446, Nov. 5, 2014.*
Kinnula et al., Free Radical Biology and Medicine 36(6):718-744, 2004.*
GenBank: CP014783.1, Mar. 23, 2016, 980 pages.
Inaoka, T. et al., "Molecular Cloning and Nucleotide Sequence of the Superoxide Dismutase Gene and Characterization of Its Product from Bacillus subtilis", Journal of Bacteriology, Jul. 1998, vol. 180, No. 14, pp. 3697-3703.
Carillon, J. et al., "Superoxide Dismutase Administration, A Potential Therapy Against Oxidative Stress Related Diseases: Several Routes of Supplementation and Proposal of an Original Mechanism of Action", Pharmaceutical Research, 2013, vol. 30, pp. 2718-2728.

(Continued)

*Primary Examiner* — Delia M Ramirez
(74) *Attorney, Agent, or Firm* — Hamre, Schumann, Mueller & Larson, P.C.

(57) ABSTRACT

The present invention relates to a *Bacillus amyloliquefaciens* strain that produces superoxide dismutase (SOD), and also relates to an antioxidant, anti-inflammatory pharmaceutical composition and a pharmaceutical composition and food composition for preventing or treating hyperlipidemia, which include a superoxide dismutase produced by the *Bacillus amyloliquefaciens* strain. The compositions of the present invention exhibit excellent effects without causing side effects, and may thus be used as functional raw materials or products having an enhanced activity of preventing or treating inflammation, cancer or hyperlipidemia in the pharmaceutical drug, food, cosmetic and livestock fields.

2 Claims, 9 Drawing Sheets

Specification includes a Sequence Listing.

(56) References Cited

OTHER PUBLICATIONS

Decorde, K. et al., "An SOD rich melon extract Extramel prevents aortic lipids and liver steatosis in diet-induced model of atherosclerosis", Nutrition, Metabolism & Cardiovascular Diseases, 2010, vol. 20, pp. 301-307.

Fang, X. et al., "Overexpression of Human Superoxide Dismutase Inhibits Oxidation of Low-Density Lipoprotein by Endothelial Cells", Circulation Research, 1998, vol. 82, pp. 1289-1297.

International Search Report and Written Opinion issued for PCT/KR2018/002677, dated Jul. 25, 2018, 11 pages.

* cited by examiner

[Fig. 1]
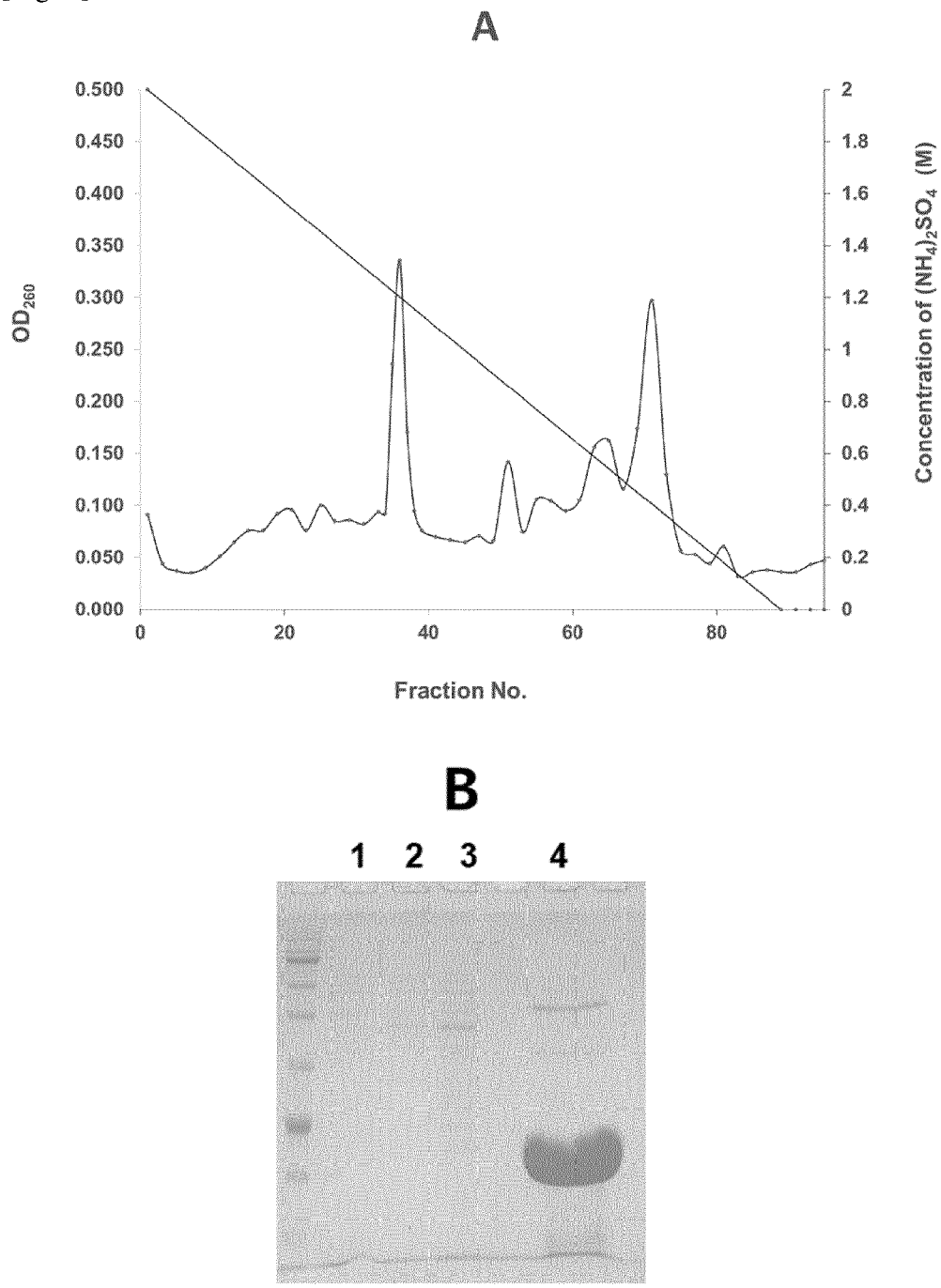
1. Culture supernatant of seed culture
2. Culture supernatant of main culture
3. UF concentrate
4. Concentrate of purified SOD

[Fig. 2]
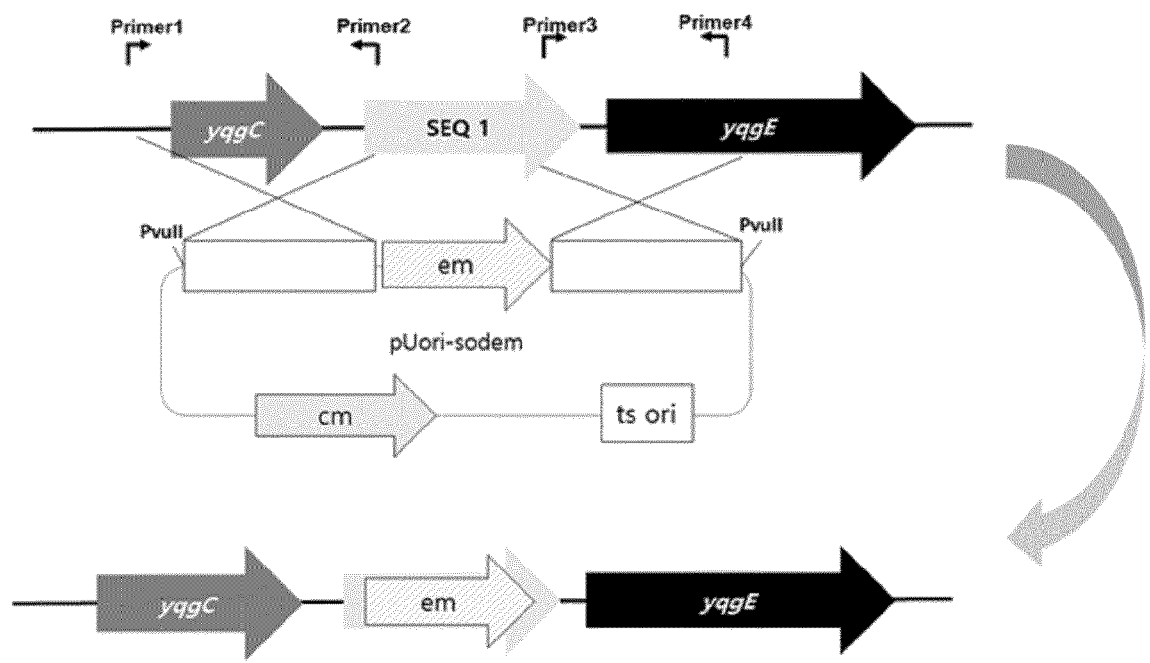

[Fig. 3]
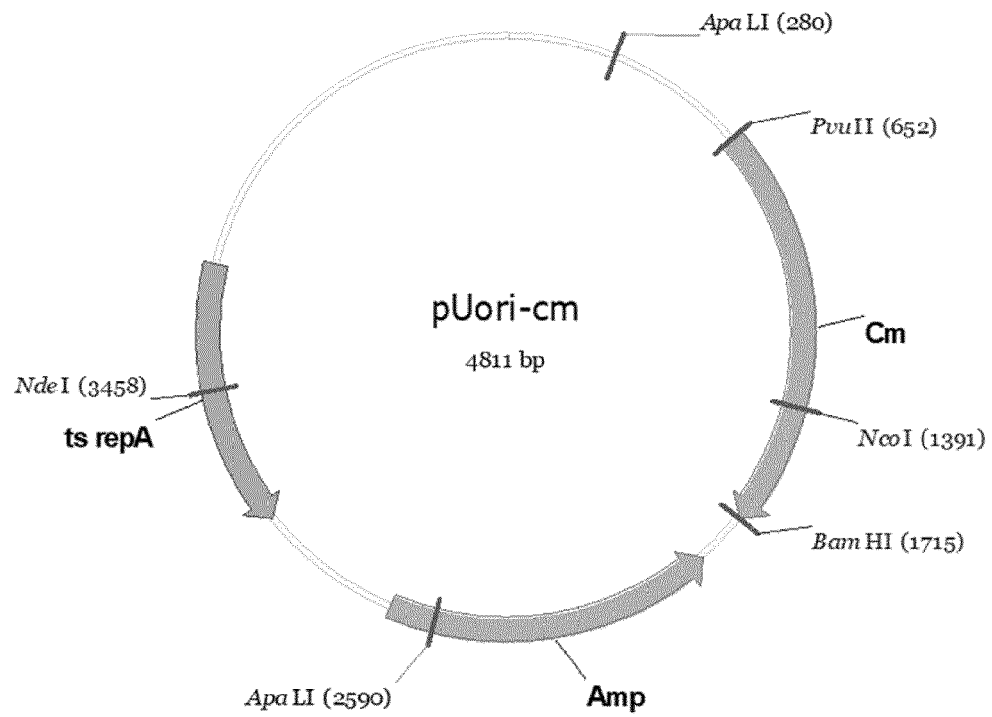
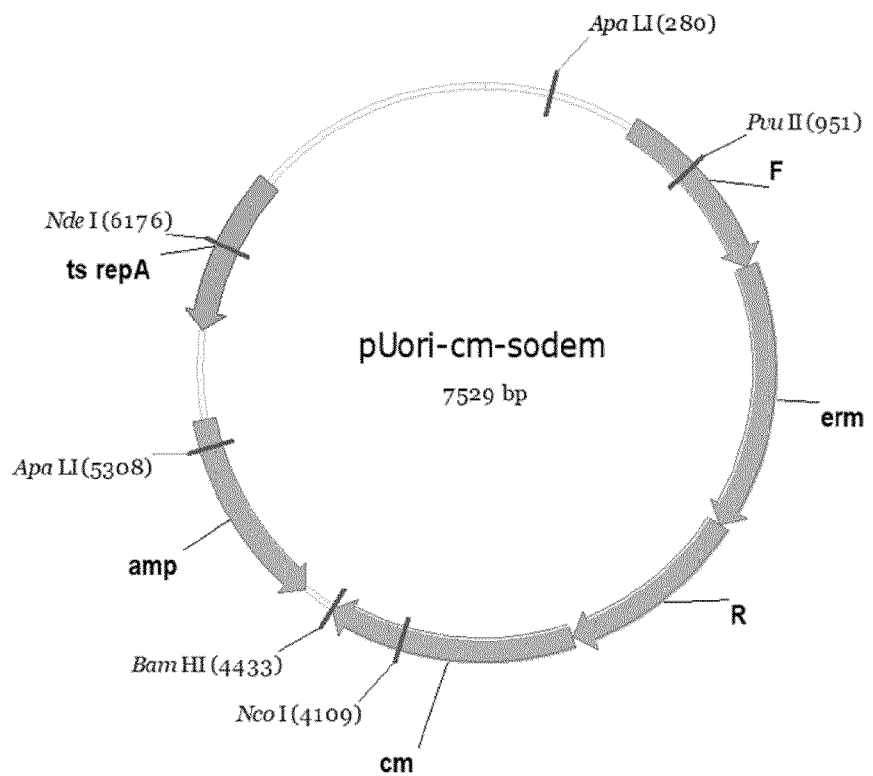

[Fig. 4]
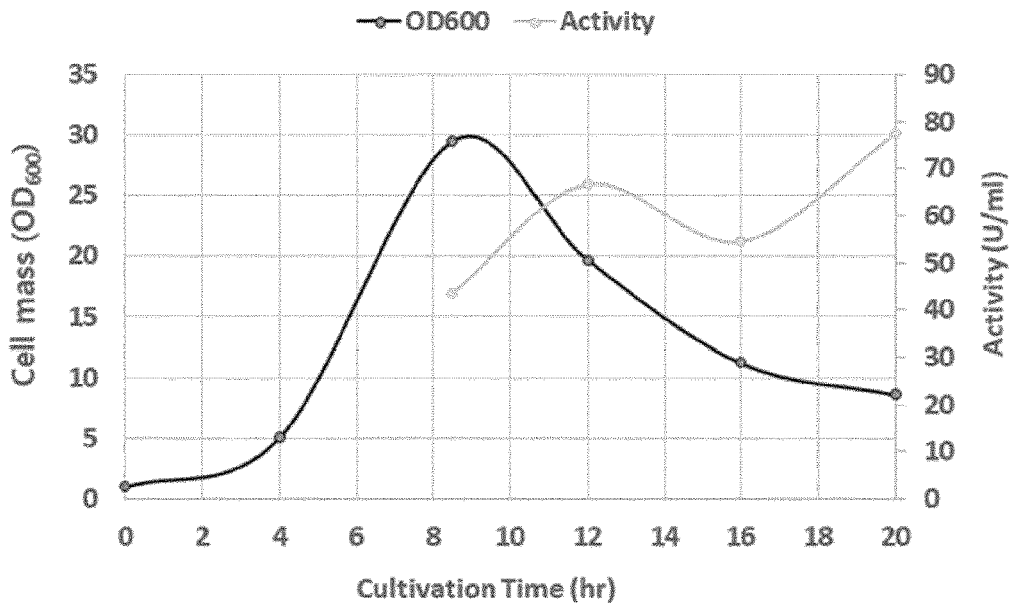
[Fig. 5]
[Fig. 6A]
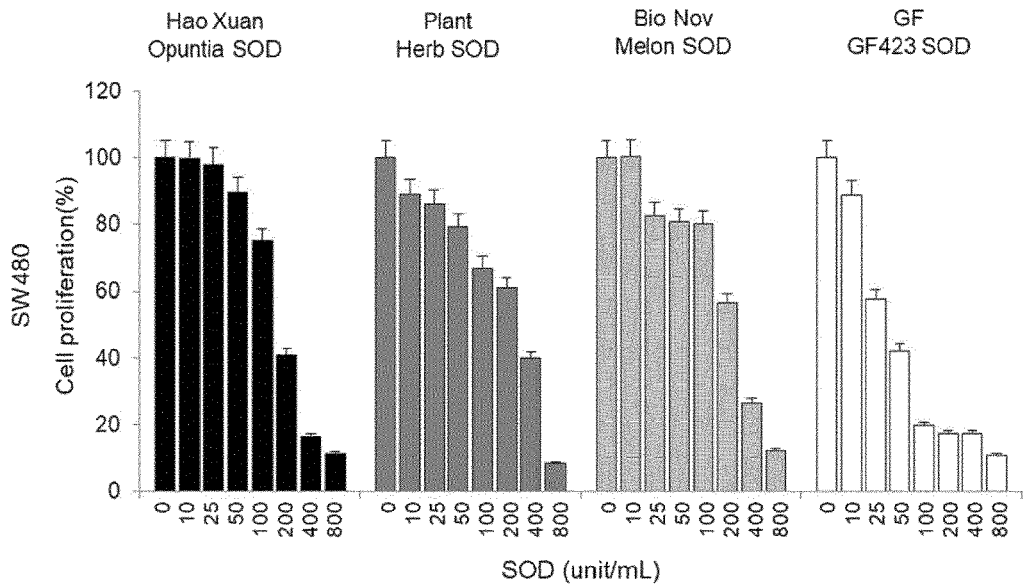

[Fig. 6B]
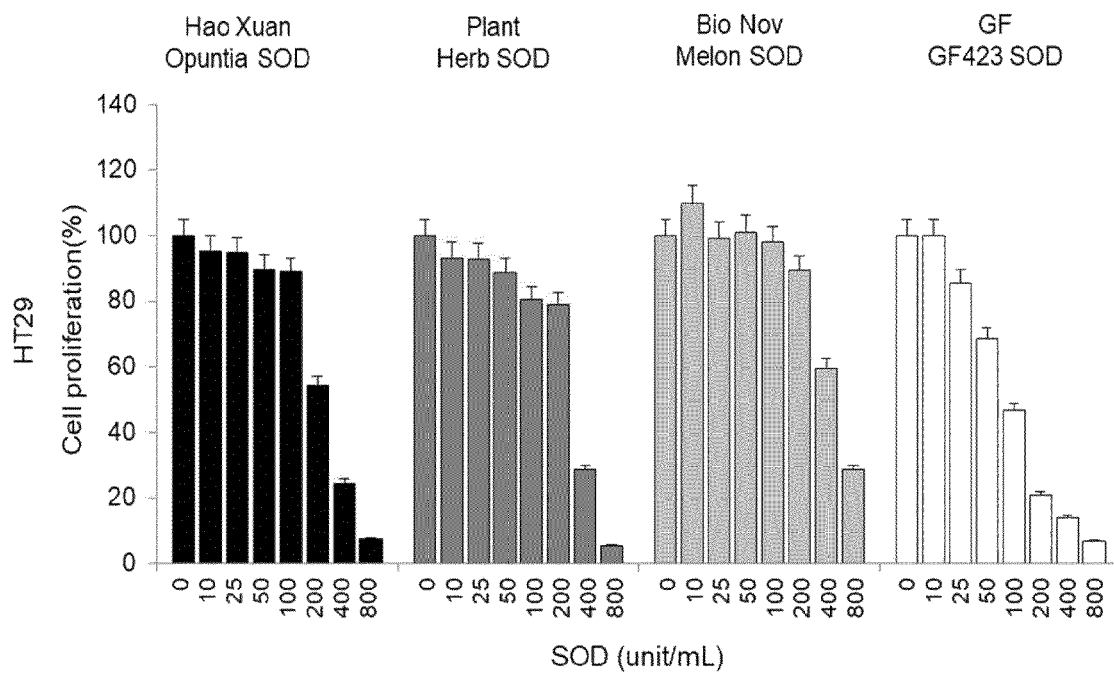
[Fig. 7]
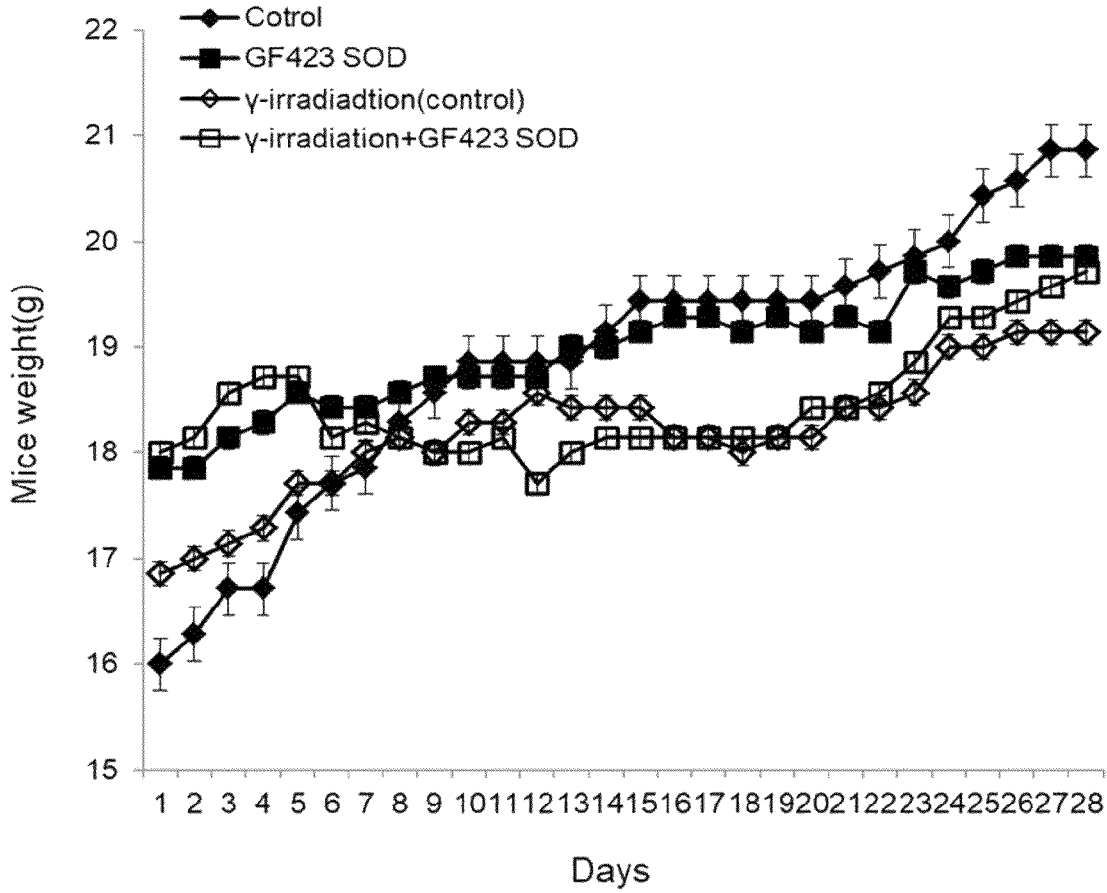

[Fig. 8]
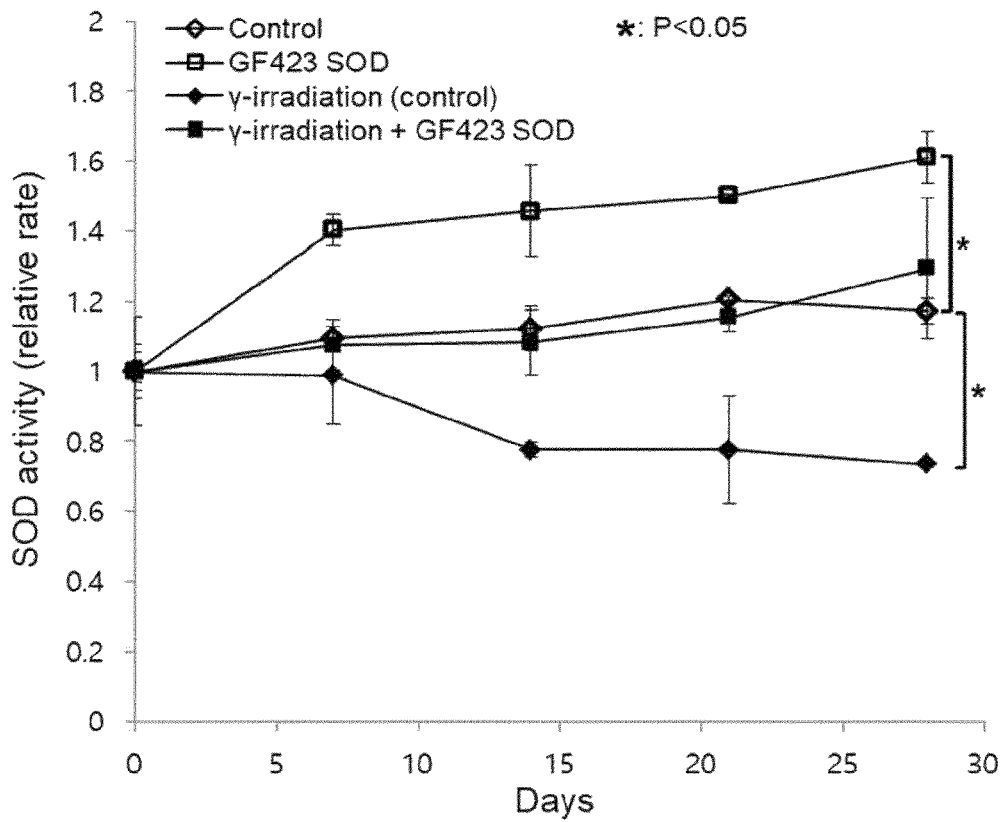
[Fig. 9]
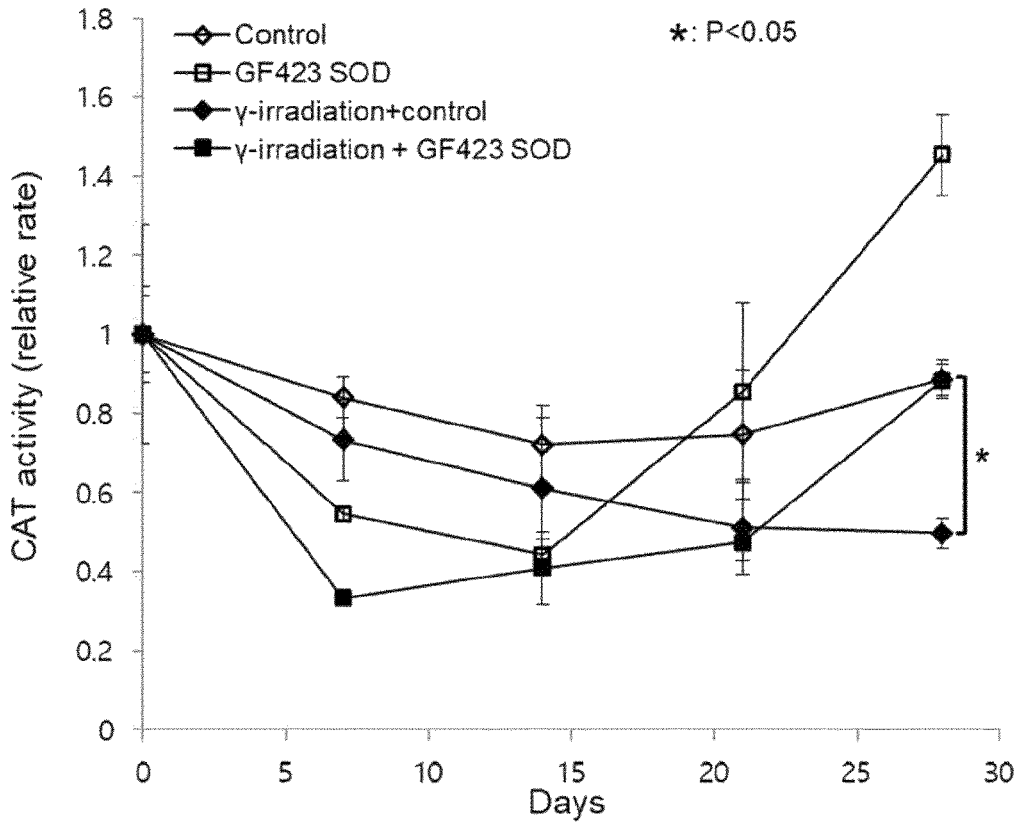

[Fig. 10]
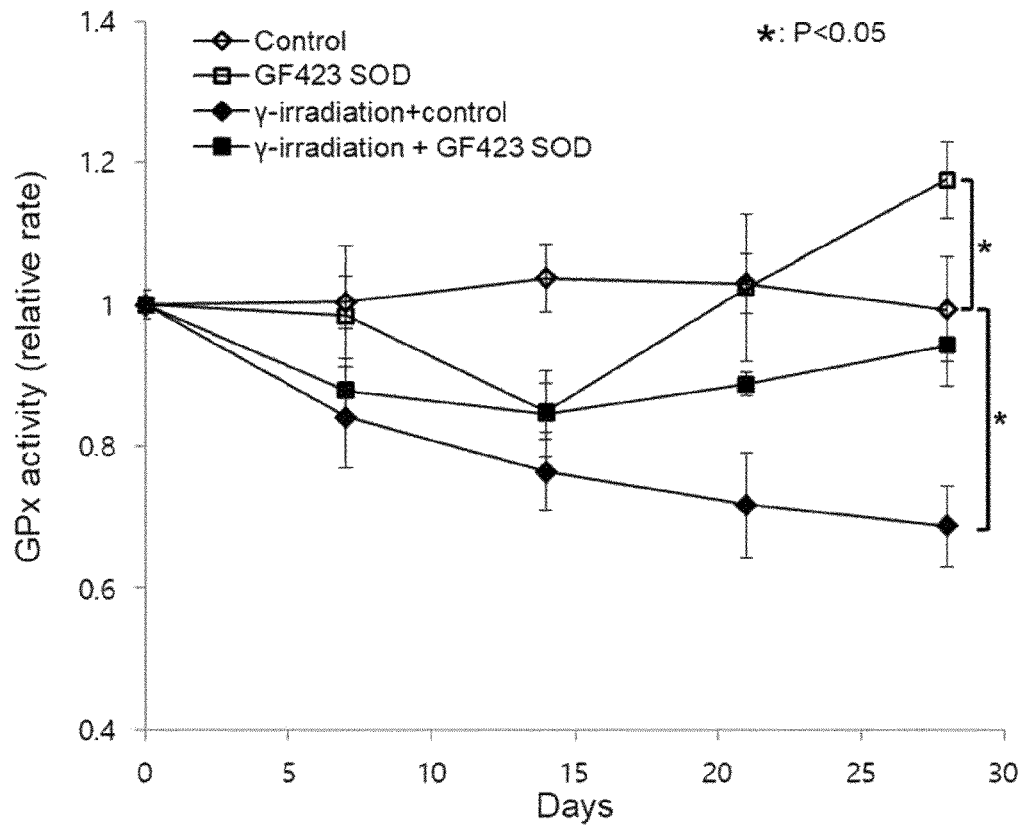
[Fig. 11]
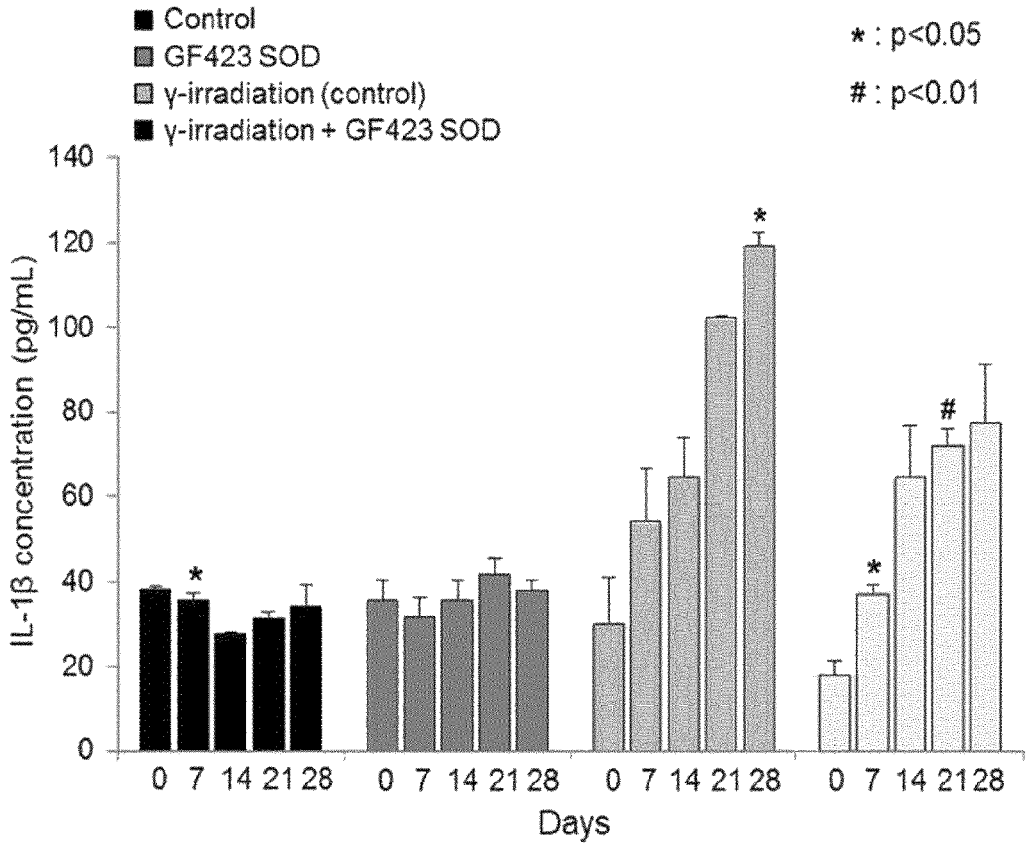

[Fig. 12]
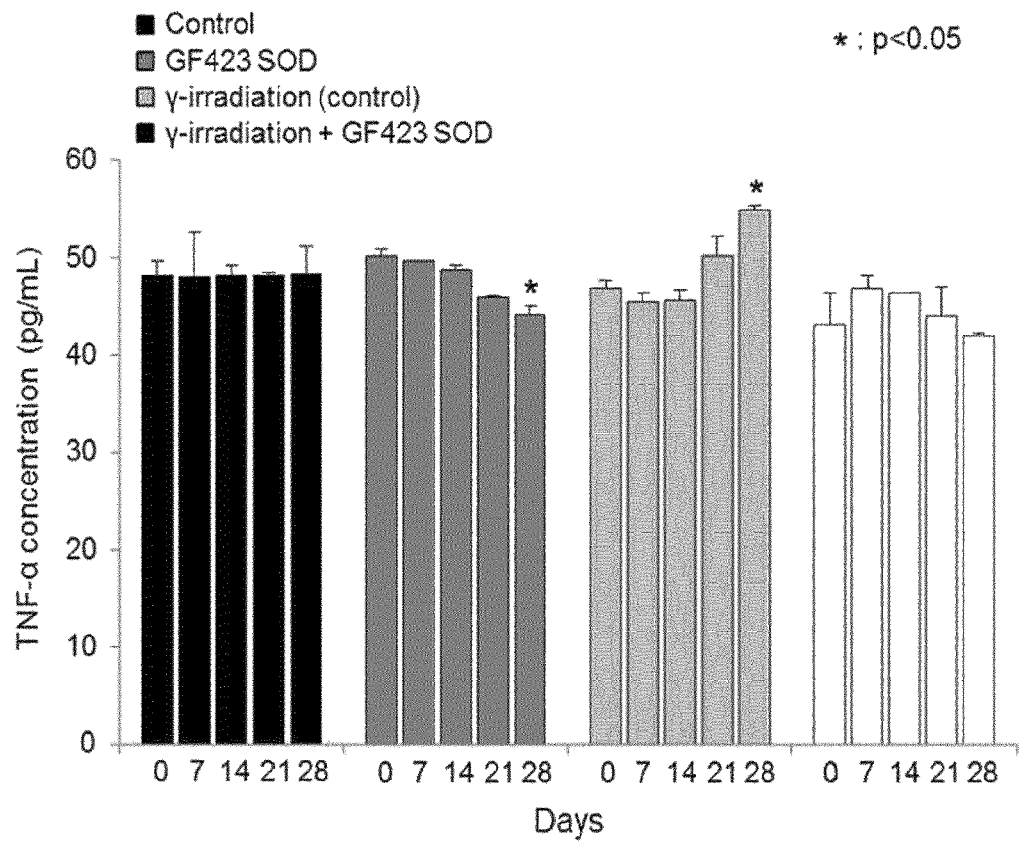
[Fig. 13]
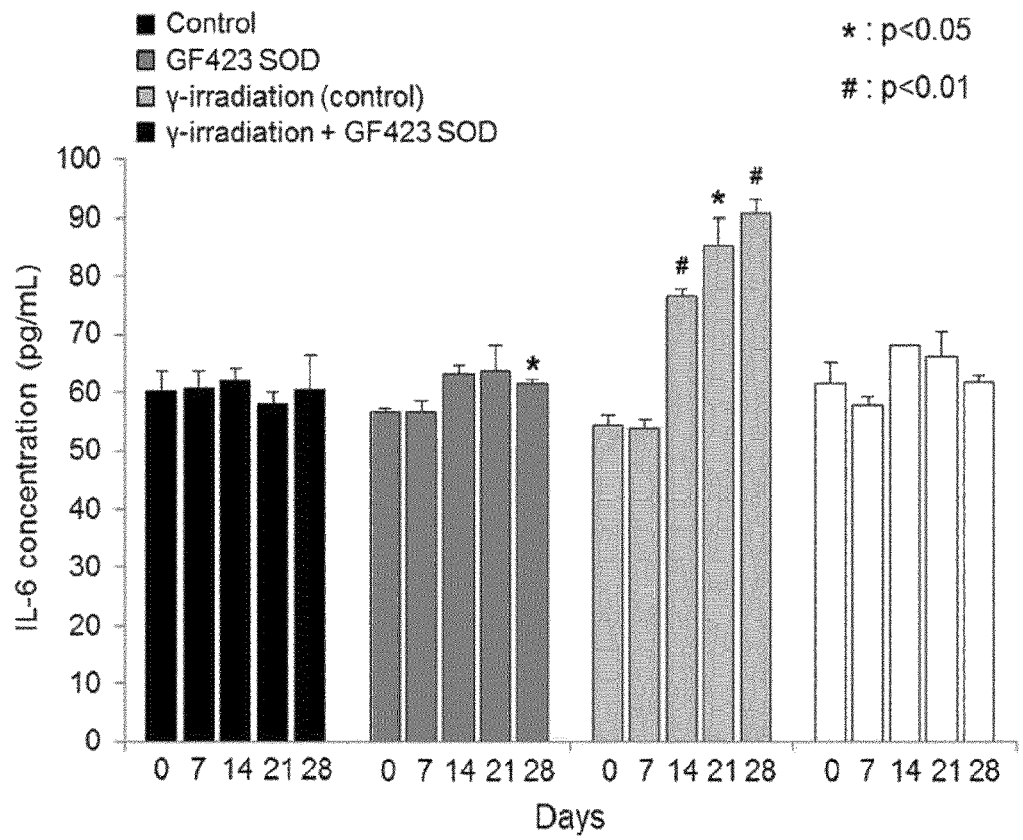

[Fig. 14]
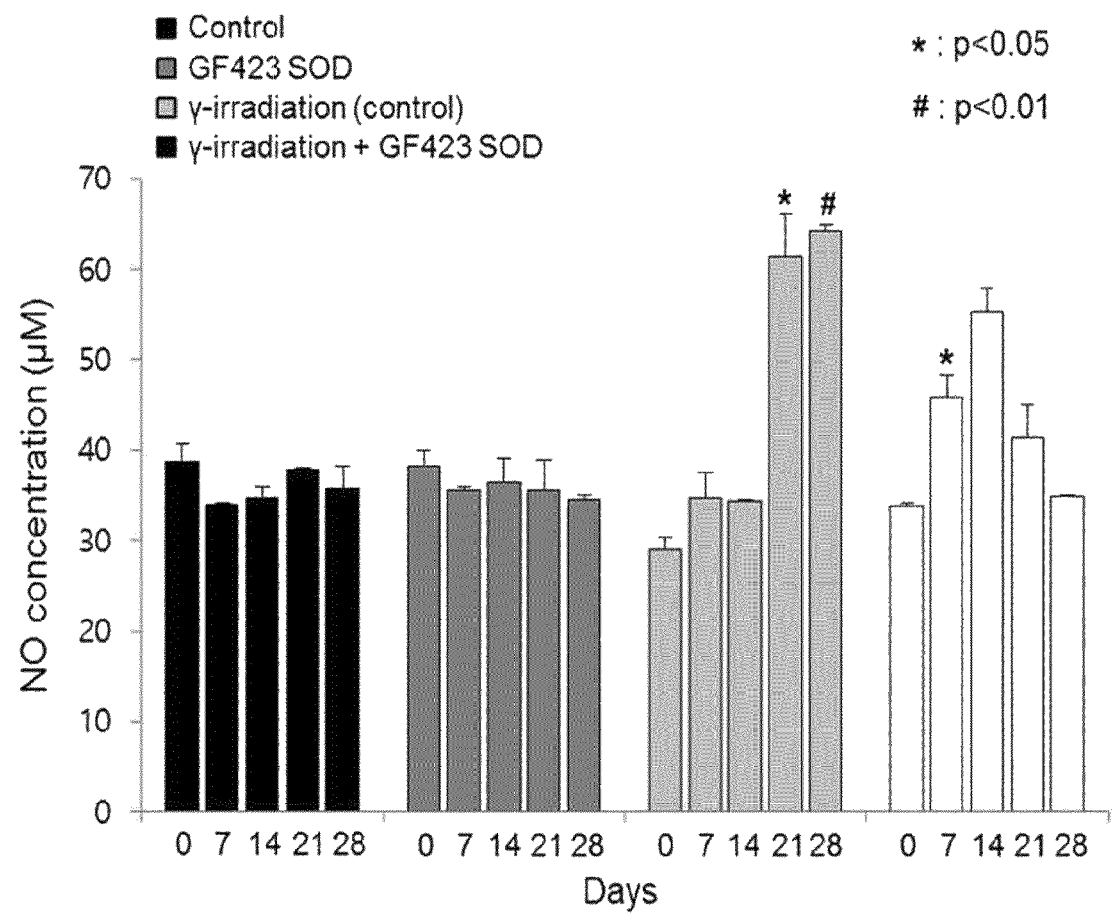

BACILLUS AMYLOLIQUEFACIENS GF423 STRAIN, AND COMPOSITION FOR PROVIDING ANTIOXIDANT AND ANTI-INFLAMMATORY ACTIVITIES OR PREVENTING OR TREATING HYPERLIPIDEMIA, INCLUDING POLYPEPTIDE PRODUCED BY THE SAME

TECHNICAL FIELD

The present invention relates to a *Bacillus amyloliquefaciens* GF423 strain, and also relates to a pharmaceutical composition and food composition for providing antioxidant and anti-inflammatory activities or preventing or treating hyperlipidemia, which include a polypeptide produced by the strain and having superoxide dismutase activity.

BACKGROUND ART

Reactive oxygen species are produced by biological reactions during normal metabolic processes in the human body. However, the accumulation of reactive oxygen species or the production of excessive amounts of reactive oxygen species is harmful to most organisms, and this condition is known as oxidative stress. Oxidative stress is known to cause various diseases in cells and tissues. As known so far, gastrointestinal diseases, diabetes, cancer, cardiovascular diseases, neurodegenerative diseases, and the like are caused by oxidative stress. As a physiological action that inhibits the production of free radicals in vivo in order to prevent this oxidative stress, the mechanism of action that donates electrons to oxidative free radicals to inhibit oxidation or to convert superoxide anion radicals into normal oxides is known.

As this oxidative stress was found to be an important factor that causes various diseases including aging, studies have been actively conducted to develop antioxidant agents that remove reactive oxygen species in vivo. Many studies have been conducted on antioxidant enzymes, such as superoxide dismutase (SOD), catalase, peroxidase, glutathione and the like, which are capable of controlling reactive oxygen species, and low molecular antioxidant substances, such as vitamin C (ascorbic acid), vitamin E (tocopherol) and the like, which are derived from natural materials. In addition, many synthetic antioxidants, such as BHA (butylatedhydroxyanisole), BHT (butylatedhydroxytoluene) and NDGA (nordihydroguaiaretic acid), have also been developed and used in the pharmaceutical and food fields.

However, natural antioxidant substances derived from natural materials have problems in that, because these antioxidant substances do not have potent antioxidant effects, they should be used in large amounts in order to provide substantial antioxidant effects, and accordingly the use of these antioxidant substances is expensive and has low economic efficiency. Meanwhile, although chemically synthesized antioxidant substances exhibit excellent antioxidant effects compared to the natural antioxidant substances, they have a new problem in that serious and mild side effects are caused in the humanbody, and thus the use thereof is limited.

Meanwhile, the excessive accumulation of lipids on blood vessel walls reduces the size of blood vessels, and causes atherosclerosis through inflammatory responses. This can cause coronary heart diseases, cerebrovascular diseases, peripheral vascular occlusion, or the like. In addition, excessive blood lipids can accumulate in liver tissue, causing fatty liver.

Methods used so far to reduce blood lipid levels include a dietary therapy that reduces the intake of foods containing large amounts of cholesterols or fats, as well as exercise therapy and drug therapy. However, dietary therapy or exercise therapy is difficult to manage strictly and implement, and the therapeutic effect thereof is also limited.

Meanwhile, drugs that have been developed so farto reduce lipid levels include: bile acid binding resins; cholesterol level-lowering drugs, such as inhibitors of HMF-CoA reductase, which is an enzyme important in cholesterol synthesis; and triglyceride lowering drugs, such as fabric acid derivatives, nicotinic acid, etc. However, these drugs were reported to cause side effects, including hepatotoxicity, gastrointestinal disorders, carcinogenesis, and the like. Accordingly, there is an urgent need to develop drugs which may be used to treat hyperlipidemia and related diseases by effectively lowering blood lipid levels and which cause less side effects.

DISCLOSURE OF INVENTION

Technical Problem

Under the above background, the present inventors have made extensive efforts to develop an antioxidant substance which ensures its safety because it is derived from a natural source and which also exhibits excellent antioxidant effects. As a result, the present inventors have found that an extract from a *Bacillus amyloliquefaciens* strain exhibits excellent superoxide dismutase activity, thereby completing the present invention.

Another object of the present invention is to provide a method for producing SOD using the above-described superoxide dismutase.

Another object of the present invention is to provide an antioxidant and anti-inflammatory pharmaceutical composition including an SOD produced by a *Bacillus amyloliquefaciens* GF423 strain and including an amino acid sequence of SEQ ID NO: 2.

Still another object of the present invention is to provide a functional health food and feed additive having antioxidant and anti-inflammatory activities, which include an SOD produced by a *Bacillus amyloliquefaciens* GF423 strain and including an amino acid sequence of SEQ ID NO: 2.

Still another object of the present invention is to provide a means for preventing or treating a disease or disorder related to lipid metabolism abnormalities, which is safe without toxic side effects, specifically a pharmaceutical composition for preventing or treating hyperlipidemia.

Yet another object of the present invention is to provide a functional health food for preventing or improving hyperlipidemia, which includes an SOD produced by a *Bacillus amyloliquefaciens* GF423 strain and including an amino acid sequence of SEQ ID NO: 2.

Solution to Problem

One aspect of the present invention for accomplishing the above objects is directed to a *Bacillus amyloliquefaciens* GF423 strain which produces a polypeptide having superoxide dismutase (SOD) activity and which has been internationally deposited with the Korean Collection for Type Culture (KCTC) under accession number KCTC 13222BP.

Another aspect of the present invention is directed to a method for producing a polypeptide having superoxide dismutase (SOD) activity, the method including isolating a polypeptide having superoxide dismutase (SOD) activity from a culture obtained by culturing a *Bacillus amyloliquefaciens* GF423 strain which has been internationally deposited with the Korean Collection for Type Culture (KCTC) under accession number KCTC 13222BP.

Still another aspect of the present invention is directed to an antioxidant and anti-inflammatory pharmaceutical composition including an SOD produced by a *Bacillus amyloliquefaciens* GF423 strain which has been internationally deposited with the Korean Collection for Type Culture (KCTC) under accession number KCTC 13222BP, the SOD including an amino acid sequence of SEQ ID NO: 2.

Still another aspect of the present invention is directed to an antioxidant or anti-inflammatory functional health food, the functional health food including an SOD produced by a *Bacillus amyloliquefaciens* GF423 strain, the SOD including an amino acid sequence of SEQ ID NO: 2.

Still another aspect of the present invention is directed to a pharmaceutical composition for preventing or treating hyperlipidemia, which includes a superoxide dismutase produced by a *Bacillus amyloliquefaciens* GF423 strain which has been internationally deposited with the Korean Collection for Type Culture (KCTC) under accession number KCTC 13222BP, the superoxide dismutase including an amino acid sequence of SEQ ID NO: 2.

Yet another aspect of the present invention is directed to a functional health food for preventing or improving hyperlipidemia, the food including a superoxide dismutase produced by a *Bacillus amyloliquefaciens* GF423 strain which has been internationally deposited with the Korean Collection for Type Culture (KCTC) under accession number KCTC 13222BP, the superoxide dismutase including an amino acid sequence of SEQ ID NO: 2.

Advantageous Effects of Invention

The *Bacillus amyloliquefaciens* strain according to the present invention has very high superoxide dismutase productivity, and can thus be advantageously used for the production of materials for foods, functional health foods, health supplement foods, pharmaceutical drugs, and cosmetic products.

The strain of the present invention is a microorganism which is safe for humans, and SOD is an enzyme which is secreted extracellularly. Accordingly, when SOD is produced using the strain according to the present invention, SOD whose safety to humans is ensured may be produced in large amounts without requiring an expensive purification process (e.g., column chromatography purification). In addition, when SOD is produced by culturing the strain according to the present invention, the culturing time is shorter than that in the production of SOD from plants, and a space required for SOD production is significantly smaller than that required for plant cultivation, thereby enabling SOD to be economically produced.

Unlike other plant-derived superoxide dismutases which are currently commercially available, the *Bacillus amyloliquefaciens*-derived polypeptide having superoxide dismutase activity according to the present invention is produced by extracellular secretion, and thus the stability of enzymatic activity thereof is excellent. In addition, the polypeptide according to the present invention has better antioxidant effects than conventional natural antioxidant substances, and exhibits antioxidant effects comparable to those of synthetic antioxidant substances. Accordingly, the polypeptide according to the present invention may be widely used for the development of various products, such as foods, functional health foods, pharmaceutical drugs, cosmetic products and the like, which include antioxidant substances.

The composition according to the present invention has antioxidant activity and exhibits better anti-inflammatory effects by inhibiting the production and secretion of inflammatory inducers and reactive oxygen species and the expression of inflammatory mediators and inflammatory inducers during inflammatory responses.

The antioxidant and anti-inflammatory composition according to the present invention has an excellent ability to eliminate superoxide anion radicals, and also exhibits a very excellent effect of inhibiting lipid oxide production. Accordingly, the application of this composition to cosmetic compositions is effective in skin aging inhibition and skin whitening.

The pharmaceutical composition according to the present invention can be effectively used for the treatment of hyperlipidemia and related diseases, and thus can be used for the prevention or treatment of coronary heart disease, cerebrovascular disease, peripheral vascular occlusion or the like, which are caused by high levels of lipids in blood vessels.

The pharmaceutical composition according to the present invention includes a superoxide dismutase derived from a *Bacillus amyloliquefaciens* strain, and thus has ensured safety and also a remarkable and advantageous effect on the inhibition of lesions that may be caused by hyperlipidemia. Accordingly, the pharmaceutical composition can be widely used for the development of various pharmaceutical drugs, functional health foods, feed additives, or the like.

BRIEF DESCRIPTION OF DRAWINGS

FIG. 1 is a graph showing the results of purifying superoxide dismutase (SOD) from a *Bacillus amyloliquefaciens* GF423 strain by phenyl-sepharose elution according to an example of the present invention;

FIG. 2 is a view illustrating a method of inactivating the SOD gene from a *Bacillus amyloliquefaciens* GF423 strain;

FIG. 3 is a schematic view showing plasmids used to inactivate the SOD gene from a *Bacillus amyloliquefaciens* GF423 strain;

FIG. 4 is a view showing the results of comparing amino acid sequence homology between an SOD produced by a *Bacillus amyloliquefaciens* GF423 strain of the present invention and melon SOD;

FIG. 5 is a graph showing the cultivation pattern of a *Bacillus amyloliquefaciens* GF423 strain;

FIGS. 6A and 6B are graphs showing the effect of a polypeptide of the present invention, produced by a *Bacillus amyloliquefaciens* GF423 strain and having SOD activity, on the proliferation of colorectal cancer cells;

FIG. 7 is a graph showing the effect of an SOD, produced by a *Bacillus amyloliquefaciens* GF423 strain of the present invention, on the weight change of mice;

FIG. 8 is a graph showing the effect of an SOD, produced by a *Bacillus amyloliquefaciens* GF423 strain of the present invention, on superoxide dismutase (SOD) activity in mouse blood;

FIG. 9 is a graph showing the effect of an SOD, produced by a *Bacillus amyloliquefaciens* GF423 strain of the present invention, on mouse catalase (CAT) activity;

FIG. 10 is a graph showing the effect of an SOD, produced by a *Bacillus amyloliquefaciens* GF423 strain of the present invention, on glutathione peroxidase (GPx) activity in mouse blood;

FIG. 11 is a graph showing the effect of an SOD, produced by a *Bacillus amyloliquefaciens* GF423 strain of the present invention, on the concentration of inflammatory cytokine IL-1β in mouse blood;

FIG. 12 is a graph showing the effect of an SOD, produced by a *Bacillus amyloliquefaciens* GF423 strain of the present invention, on the concentration of inflammatory cytokine TNF-α in mouse blood;

FIG. 13 is a graph showing the effect of an SOD, produced by a *Bacillus amyloliquefaciens* GF423 strain of the present invention, on the concentration of inflammatory cytokine IL-6 in mouse blood; and FIG. 14 is a graph showing the effect of an SOD, produced by a *Bacillus amyloliquefaciens* GF423 strain of the present invention, on the concentration of nitric oxide (NO) in mouse blood.

BEST MODE FOR CARRYING OUT THE INVENTION

The present invention will be described in greater detail below with reference to the accompanying drawings.

As used herein, the term "antioxidant" means, in a narrow sense, an action of inhibiting, reducing or controlling the production of free radicals in the body, hydrogen peroxide or peroxides from the free radicals, and hydroxyl radicals from the hydrogen peroxide, and means, in a broad sense, an action of inhibiting, reducing or controlling naturally occurring oxidation reactions.

As used herein, the term "nucleicacid molecules" is intended to comprehensively include DNA (gDNA and cDNA) and RNA molecules. Nucleotides which are the basic units of the nucleicacid molecules include not only natural nucleotides but also analogue having modified sugar or base moieties (Scheit, Nucleotide Analogs, John Wiley, New York(1980); Uhlman and Peyman, Chemical Reviews, 90:543-584(1990)).

As used herein, the term "anti-inflammatory" is defined as an activity of alleviating the inflammatory diseases defined below, and "alleviating" is intended to include the alleviation of pathological symptoms of inflammatory diseases and the inhibition and retardation of development of such pathological symptoms. As used herein, the term "inflammatory diseases" may be defined as any morbid conditions specified by local or systemic defense responses against external physical/chemical stimuli or infections with foreign infectious agents. The inflammatory diseases may be acute, chronic, ulcerative, allergic or necrotic. More specifically, the inflammatory diseases may include asthma, bronchitis, rhinitis, gastritis, enteritis, nephritis, hepatitis, pancreatitis, conjunctivitis, iritis, scleritis, uveitis, dermatitis, arthritis, and the like.

As used herein, the term "anticancer" is defined as an activity of alleviating colorectal cancer, and "alleviating" is intended to include the alleviation of pathological symptoms of colorectal cancer and the inhibition and retardation of development of such pathological symptoms.

As used herein, the term "hyperlipidemia" means a condition in which lipids, such as free cholesterols, cholesterol esters, phospholipids, triglycerides or the like, are abnormally increased. Hyperlipidemia is a condition in which the serum level of one or more of serum lipids, including cholesterol, triglyceride, phospholipid, free fatty acids and the like, is higher than 50-150 mg/dl for triglycerides, 150-250 mg/dl for phospholipids, 130-220 mg/dl for cholesterols, and 5-10 mg/dl for free fatty acids, which are normal serum lipid levels in a fasting state.

As used herein, the term "functional health food" is the same as food for special health use (FoSHU), and refers to a food having high medicinal and medical effects, which is processed to effectively exert a body-regulating function as well as to supply nutrients. In some cases, the term "functional health food" may be used interchangeably with terms such as health food, functional food, health supplement food and the like. For the purpose of the present invention, the functional health food may exhibit antioxidant, anti-inflammatory and anti-hyperlipidemia activities so as to provide useful effects that help maintain, improve or restore the health of an individual taken with the same.

One aspect of the present invention is directed to a *Bacillus amyloliquefaciens* GF423 strain which produces a polypeptide having superoxide dismutase (SOD) activity. This strain of the present invention was isolated from Bispan powder purchased from Binex Co., Ltd, and has an excellent ability to produce SOD. The *Bacillus amyloliquefaciens* GF423 strain was internationally deposited with the Korean Collection for Type Culture (KCTC) on Mar. 6, 2017 under accession number KCTC 13222BP.

The *Bacillus amyloliquefaciens* strain of the present invention produces a polypeptide having superoxide dismutase (SOD) activity, which is encoded by a nucleotide sequence represented by SEQ ID NO: 1. This polypeptide having SOD activity has an amino acid sequence of SEQ ID NO: 2.

The strain of the present invention has the same 16S ribosomal RNA nucleotide sequences as SEQ ID NOs: 3 to 11.

The characteristics of the *Bacillus amyloliquefaciens* GF423 strain according to the present invention are as follows:

TABLE 1

| 1) Characteristics of bacteria | |
|---|---|
| | Characteristics of bacteria when cultured on LB agar plate medium at 37° C. for 2 days ① Cell morphology: *bacillus* ② Mobility: present ③ Spore forming ability: endospore formation |
| 2) Morphology of colonies | |
| | Morphology of colonies when cultured on LB agar plate medium at 37° C. for 2 days ① Shape: circular ② Ridge: convex ③ surface: smooth |
| 3) Physiological properties | |
| | ① Growth temperature: possible growth temperature 15 to 40° C. Optimal growth temperature 37° C. ② Growth pH: possible growth pH 5.0 to 7.5 Optimal pH 6.0 to 6.5 ③ Effect on oxygen: anaerobic |
| 4) Catalase | − |
| 5) Gas formation | − |
| 6) Growth at 15° C. | − |
| 7) Growth at 45° C. | + |
| 8) Indole production | − |
| 9) Lactic acid production | + |

The sugar utilization of the *Bacillus amyloliquefaciens* GF423 strain according to the present invention is as follows:

TABLE 2

| Carbohydrate | Utilized | Carbohydrate | Utilized |
|---|---|---|---|
| Glycerol | − | Escune | + |
| Erythritol | − | Salicine | + |
| D-Arabinose | − | Cellobiose | + |
| L-Arabinose | − | Maltose | − |
| Ribose | − | Lactose | − |
| D-Xylose | − | Melibiose | − |
| L-Xylose | − | Saccharose | + |
| Adonitol | − | Trehalose | + |
| b-Mlethyl-xyloside | − | Inuline | − |
| Galactose | − | Melezitose | − |
| D-glucose | + | D-raffinose | − |
| D-gructose | + | Amidon | − |
| D-mannose | + | Glycogene | − |
| L-sorbose | − | Xylitol | − |
| Rhamnose | − | b-gentiobiose | − |
| Dulcitol | − | D-Turanose | − |
| Inositol | − | D-Lyxose | − |
| Mannitol | − | D-Tagatose | − |
| Sorbitol | + | D-Fucose | − |
| a-Methyl-D-mannoside | − | L-Fucose | − |
| a-Methyl-D-glucoside | − | D-arabitol | − |
| N-Acetyl glucosamine | − | L-arabitol | − |
| Amygdaline | − | Gluconate | − |
| Arbutine | + | 2-ceto-gluconate | − |
| | | 5 ceto-gluconate | − |

In accordance with another aspect, the present invention provides a method for producing a polypeptide having superoxide dismutase (SOD) activity, the method including the step of isolating a polypeptide having superoxide dismutase (SOD) activity from a culture obtained by culturing a Bacillus amyloliquefaciens GF423 strain which produces the polypeptide having superoxide dismutase (SOD) activity and which has been internationally deposited with the Korean Collection for Type Culture (KCTC) under accession number KCTC 13222BP.

The culturing of the Bacillus amyloliquefaciens GF423 strain of the present invention may be performed using a suitable medium and culture conditions known in the art. This culturing process may be easily controlled by any person skilled in the art depending on the selected strain. Examples of the culturing method include, but are not limited to, batch culture, continuous culture and fed-batch culture. Such culture methods are described in, for example, "Biochemical Engineering" by James M. Lee, Prentice-Hall International Editions, pp. 138-176.

A medium that is used in culturing of the strain of the present invention should satisfy the conditions required for a specific strain. Various microbial culture media are described in, for example, "Manual of Methods for General Bacteriology" by the American Society for Bacteriology, Washington D.C., USA, 1981. These media include a variety of carbon sources, nitrogen sources and trace element ingredients. The carbon sources include carbohydrates such as glucose, sucrose, lactose, fructose, maltose, starch and cellulose; fats such as soybean oil, sunflower oil, castor oil and coconut oil; fatty acids such as palmitic acid, stearic acid, and linoleic acid; alcohols such as glycerol and ethanol; and organic acids such as acetic acid. These carbon sources are used alone or in combination. The nitrogen sources include organic nitrogen sources such as peptone, yeast extract, gravy, malt extract, corn steep liquor (CSL), and soybean flour; and inorganic nitrogen sources such as urea, ammonium sulfate, ammonium chloride, ammonium phosphate, ammonium carbonate, and ammonium nitrate. These nitrogen sources may be used alone or in combination. The medium may further include, as phosphorus sources, potassium dihydrogen phosphate, potassium hydrogen phosphate and the corresponding sodium-containing salts. In addition, the medium may include metal salts such as magnesium sulfate or iron sulfate. In addition, the culture medium may include amino acids, vitamins and suitable precursors. These media or precursors may be added to the culture in a batchwise or continuous manner.

In addition, the pH of the culture may be adjusted by adding compounds such as ammonium hydroxide, potassium hydroxide, ammonia, phosphoric acid and sulfuric acid in a suitable manner during culturing. In addition, to inhibit the production of foam during culturing, anti-foaming agents such as fatty acid polyglycol esters may be used. In order to maintain the culture under aerobic conditions, oxygen or oxygen-containing gas (e.g., air) may be passed into the culture. The temperature of the culture generally ranges from 20 to 45° C., preferably 25 to 40° C. The culture procedure may be continued until the production of a polypeptide having SOD activity reaches a desired level. Preferably, the culturing time is 48 to 72 hours.

The polypeptide having SOD activity is preferably isolated by the following method, but is not limited thereto. A culture obtained by culturing the Bacillus amyloliquefaciens GF423 strain is centrifuged, and the supernatant fraction is collected, pretreated by solid phase extraction, and then separated and purified by chromatography. Here, the chromatography used is preferably hydrophobic interaction chromatography, but is not necessarily limited thereto.

The method of the present invention may further include the step of mixing a purified solution, obtained by purifying the produced polypeptide having superoxide dismutase from the host cell, with shellac-containing buffer, and freeze-drying the mixture. When SOD is administered orally, a problem may arise in that the activity of the SOD in the gastrointestinal tract decreases rapidly, leading to a reduction in the bioavailability and efficiency of the SOD. This problem becomes more severe because it is difficult to deliver the SOD to a specific position at which the effect of the SOD is the highest. For this reason, in the method of the present invention, the superoxide dismutase may be coated in a solution state. More specifically, the purified solution and mixed with shellac-containing buffer, and then freeze-dried. This freeze-dried strain sample may be powdered and stored at about −4° C. until use.

Examples of a coating suitable for use in the present invention include, but are not limited to, shellac, ethyl cellulose, hydroxypropyl methyl cellulose, hydroxypropylmethyl cellulose phthalate, zein, Eudragit, and combinations thereof.

In the present invention, the coating is preferably contained in an amount of 0.6 to 4 wt % based on the total weight of the purified SOD powder. In addition, the coating solution may further contain a plasticizer such as calcium chloride, citric acid, glycerin acetic acid fatty acid ester, polysorbate, D-sorbitol or triacetin.

Another aspect of the present invention is directed to an antioxidant and anti-inflammatory pharmaceutical composition including an SOD produced by a Bacillus amyloliquefaciens GF423 strain which has been internationally deposited with the Korean Collection for Type Culture (KCTC) under accession number KCTC 13222BP, the SOD including an amino acid sequence of SEQ ID NO: 2.

The antioxidant and anti-inflammatory pharmaceutical composition according to the present invention may inhibit radicals and lipid peroxides, which are the major cause of cell damage, and may increase the activity of intracellular antioxidant enzymes to remove reactive oxygen species, thereby preventing cell damage caused by oxidative stress, indicating that it may be used as an antioxidant drug. In addition, the antioxidant and anti-inflammatory pharmaceutical composition according to the present invention has anticancer activity against colorectal cancer cells, and thus may be used as an anticancer drug.

Still another aspect of the present invention is directed to a pharmaceutical composition for preventing or treating hyperlipidemia, which includes a superoxide dismutase produced by a *Bacillus amyloliquefaciens* GF423 strain which has been internationally deposited with the Korean Collection for Type Culture (KCTC) under accession number KCTC 13222BP, the superoxide dismutase including an amino acid sequence of SEQ ID NO: 2.

Blood low-density lipoprotein (LDL) is degraded by a receptor in cells. However, when the receptor is lacked and deficient due to the intake of large amounts of cholesterols, the blood level of LDL will increase and the LDL will accumulate to produce oxidized LDL. The oxidized LDL has highly cytotoxic lipid peroxides which diffuse to cells and tissues so as to show toxicity and cause inflammation in endothelial cells, causing arteriosclerosis. The pharmaceutical composition of the present invention may activate the antioxidant function of the body by sufficiently detoxifying reactive oxygen species, prevent or retard the development of hyperlipidemia by reducing the peroxidation rate of low-density lipoprotein, and alleviate or ameliorate hyperlipidemia by reducing blood total cholesterol, LDL cholesterol and triglyceride levels.

The pharmaceutical composition of the present invention may be used alone or in combination with other drugs in order to prevent or treat hyperlipidemia, fatty liver disease or arteriosclerosis.

According to the present invention, an SOD having antioxidant, anti-inflammatory or anti-hyperlipidemia activity may be extracted from a culture supernatant of the *Bacillus amyloliquefaciens* GF423 strain. First, the *Bacillus amyloliquefaciens* GF423 strain is cultured in a complex medium (pH 6.0 to 8.0) at 25 to 42° C. for 1 to 4 days, thereby obtaining a culture. As a complex medium for culturing the *Bacillus amyloliquefaciens* GF423 strain, LB (Luria-Bertani) medium, ISP (International *Streptomyces* Project) medium, NA (nutrient agar) medium, BHI (brain heart infusion agar) medium, SDA (sabouraud dextrose agar) medium, PDA (potato dextrose agar) medium, NB (nutrient broth) medium or the like may be used. Preferably, LB medium, ISP medium, BHI medium, SDA medium or NB medium may be used.

The culture is centrifuged to obtain a culture supernatant, after which the culture supernatant may be filtered and concentrated, thereby obtaining an optimal culture supernatant extract having antioxidant, anti-inflammatory or anti-hyperlipidemia activity.

The composition of the present invention may further include, in addition to the SOD produced by the *Bacillus amyloliquefaciens* GF423 strain, pharmaceutically acceptable conventional carriers or excipients, and may also be formulated with various additives such as a binder, a coating agent, a disintegrant, a lubricant and the like, which are generally used in the pharmaceutical field.

When the composition of the present invention is a pharmaceutical composition, it may include, in addition to the active ingredient, pharmaceutically acceptable carriers. These pharmaceutically acceptable carriers may include, but are not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose water, syrup, methyl cellulose, methylhydroxybenzoate, propylhydroxybenzoate, talc, magnesium stearate, mineral oil and the like.

Excipients that may be used in the present invention include sugars such as sucrose, lactose, mannitol, glucose and the like; and starch such as corn starch, potato starch, rice starch, partially pre-gelatinized starch and the like. Binders that may be used in the present invention include polysaccharides such as dextrin, sodium alginate, carrageenan, guargum, acacia, agar and the like; naturally occurring macromolecular substances such as tragacanth, gelatin, gluten and the like; cellulose derivatives such as hydroxypropyl cellulose, methyl cellulose, hydroxypropyl methyl cellulose, ethyl cellulose, hydroxypropyl ethyl cellulose, sodium carboxymethyl cellulose and the like; and polymers such as polyvinyl pyrrolidone, polyvinyl alcohol, polyvinyl acetate, polyethylene glycol, polyacrylic acid, polymethacrylic acid and vinyl acetate resin.

Disintegrants that may be used in the present invention include cellulose derivatives such as carboxymethyl cellulose, calcium carboxymethyl cellulose, low-substitution hydroxypropyl cellulose and the like; and starch such as sodium carboxymethyl starch, hydroxypropyl starch, corn starch, potato starch, rice starch, partially pre-gelatinized starch and the like.

Examples of lubricants that may be used in the present invention include talc, stearic acid, calcium stearate, magnesium stearate, colloidal silica, hydrous silicon dioxide, various kinds of waxes and hydrogenated oils, etc.

Coating agents that may be used in the present invention include, but are not necessarily limited to, shellac, water-insoluble polymers such as dimethylaminoethyl methacrylate-methacrylic acid copolymers, polyvinyl acetaldiethylaminoacetate, ethyl acrylate-methacrylic acid copolymers, ethyl acrylate-methyl methacrylatechlorotrimethylammonium ethyl methacrylate copolymers, ethyl cellulose, etc.; enteric polymers such as methacrylic acid-ethyl acrylate copolymers, hydroxypropylmethylcellulose phthalate, hydroxypropylmethylcellulose acetate succinate, etc.; and water-soluble polymers such as methyl cellulose, hydroxypropylmethyl cellulose, polyvinylpyrrolidone, polyethylene glycol, etc.

The pharmaceutical composition of the present invention may be formulated using pharmaceutically acceptable carriers and/or excipients and may be provided in a unit dosage form or multiple-dosage form. In this case, the formulation may be in the form of solution, suspension or emulsion or in the form of elixir, extract, powder, granule, tablet, plaster, lotion, ointment or the like.

The dose of the pharmaceutical composition including the SOD produced by the *Bacillus amyloliquefaciens* GF423 strain according to the present invention may be suitably determined in view of the purpose of treatment or prevention, the type of the patient to be treated or prevented, the patient's symptoms, weight, age or sex, etc. For example, the composition of the present invention includes, as an active ingredient, a therapeutically effective amount or sitologically effective concentration of the SOD produced by the *Bacillus amyloliquefaciens* GF423 strain of the present invention, and may preferably contain the SOD in an amount of 2 to 100 U/mg.

The pharmaceutical composition is administered by a method determined according to the severity of symptoms, and is preferably administered topically. In addition, the dose of the active ingredient in the pharmaceutical composition may vary depending on the route of administration, the severity of the disease, the patient's age, sex, weight, etc., and the pharmaceutical composition may be administered once or several times a day.

The pharmaceutical composition of the present invention may be administered by various routes. All modes of administration may be expected, and the pharmaceutical composition may be administered by, for example, orally or intrarectal, intravenous, intramuscular, intrauterine, intrathecal or intracerebroventricular injection.

Still another aspect of the present invention is directed to an antioxidant or anti-inflammatory food, the food including an SOD produced by a *Bacillus amyloliquefaciens* GF423 strain, the SOD including an amino acid sequence of SEQ ID NO: 2.

The functional health food of the present invention may be prepared by various methods known in the food field and may be prepared as any food that may be taken orally by itself or mixed with a food-acceptable carrier, excipient, diluent or the like. Preferably, it may be formulated in the form of powder, granule, tablets, pills, capsules, suspensions, emulsions, syrups, infusions, liquids, extracts, gums, teas, jellies, beverages or likes.

Still another aspect of the present invention is directed to a cosmetic composition having antioxidant or anti-inflammatory activities, the cosmetic composition including an SOD produced by a *Bacillus amyloliquefaciens* GF423 strain, the SOD including an amino acid sequence of SEQ ID NO: 2.

According to an exemplary embodiment, the cosmetic composition of the present invention may be used for the preparation of functional cosmetic products.

The functional cosmetic product of the present invention may be prepared as any conventional formulation known in the art. Preferably, it may be formulated in the form of solutions, suspensions, emulsions, pastes, gels, creams, lotions, powders, soaps, surfactant-containing cleansing oils, powder foundations, emulsion foundations, wax foundations, sprays and the like. More preferably, it may be formulated in the form of skin softener, astringent lotion, nourishing lotion, nourishing cream, massage cream, lotion, gel, essence, eye cream, cleansing cream, cleansing foam, cleansing water, pack, ointment, stick, patch, spray or powder products, but is not limited thereto.

Yet another aspect of the present invention is directed to a feed additive for enhancing antioxidant and anti-inflammatory activities, the feed additive including an SOD produced by a *Bacillus amyloliquefaciens* GF423 strain, the SOD including an amino acid sequence of SEQ ID NO: 2. To prepare the feed additive of the present invention, a culture of the strain may be may be formulated alone or together with materials for feeds, such as wheat flour, starch, diluents such as dextrin, grain, bran such as chaff and defatted rice bran, and seed cakes having high oil and fat contents.

According to the present invention, the SOD components produced by *Bacillus amyloliquefaciens* GF423 strain may function to reduce oxidative stress caused by inflammation, thereby alleviating symptoms such as weight reduction, dehydration, bloody stool and the like, which occur with the onset of colitis.

Hereinafter, the present invention will be described in detail with reference to examples. However, these examples are merely intended to illustrate the contents of the present invention, and the scope of the present invention is not limited to these examples.

EXAMPLE 1

Isolation and Identification of Strain

From Bispan purchased from Binex Co., Ltd., an SOD-producing *Bacillus amyloliquefaciens* strain of the present invention was isolated by the following procedures. 0.1 g of Bispan powder was diluted in 10 ml of saline (0.9% NaCl) and plated on an agar LB plate to form colonies. Single colonies were taken from the formed colonies and plated again on an LB agar plate. This procedure was repeated three times, thereby isolating a single strain. The isolated bacteria were bacillus-shaped gram-positive bacteria and could produce endospores.

To identify the isolated strain, the genome was purified from the isolated strain according to the method described in Sambrook, J. et al., "Molecular Cloning. A Laboratory Manual, 3rd ed.", 2001, Cold Spring Harbor Press. The nucleotide sequence of the purified genome was determined using HiSeq PE100 (Illumina).

The genome of the isolated strain was analyzed, and as a result, 9 copies of 16S rRNA genes (SEQ ID NOs: 3 to 11) were found. Among the 16S rRNA genes, BPJGP_r00130 (SEQ ID NO: 7) and BPJGP_r00160(SEQ ID NO: 8) showed the same nucleotide sequence, but other 16S rRNA genes showed different nucleotide sequences. Namely, the isolated strain had eight 16S rRNA genes having different nucleotide sequences.

Gene-level identification of the 9 copies of 16S rRNA genes was performed. The 16S rRNA database and software used were The Ribosomal Database Project's Classifier (Wang, Q. et al., Appl Environ Microbiol., 73:5261-5267 (2007)), Living Tree Project's Aligner (Pruesse, E. et al., Bioinformatics, 28:1823-1829 (2012)), and EzTaxon database's Identity (Kim, O. S. et al., Int J Syst Evol Microbiol., 62:716721 (2012)). The isolated strain was identified as a *Bacillus* sp. with a confidence of 95% or higher in the identification software.

Species-level identification of the isolated strain was performed using the EzTaxon database's Identity (Kim, O. S. et al., Int J Syst Evol Microbiol., 62:716721 (2012)). At the time, international criteria for the identity threshold of 16S rRNA for identifying species level did not exist. However, among threshold values that were most widely recognized, the highest criterion (99%) was used as a search criterion (Yarza, P. et al., Nature Rev. Microbiol., 12:635645 (2014)). In addition, because the isolated strain had 8 different 16S rRNA genes, each of the 16S rRNA genes was searched, and among the searched type strains, type strains that were commonly found were selected. As a result of the search, 80 type strains belonging to different species were found. This result is consistent with previous studies indicating that it is impossible to distinguish species belonging to the genus *Bacillus* by use of only the homology of 16S rRNA genes (Janda J. M. & Abbott S. L., J Clin Microbiol., 45:2761-2764 (2007); Maughan H. & Van der Auwera G., Infect Genet Evol., 11:789-797 (2011)).

Accordingly, genome-based classification was performed. For the strains selected in the above-described procedure, the homologies of the whole-length genomes of the isolated strains were analyzed by in silico DNA-DNA hybridization (DDH; Auch A. F. et al., Stand Genomic Sci., 28:117-234 (2010)), and type strains showing a homology of 70% or higher were selected. As a result, two standard strains were found (Table 3), and the ANI (the average nucleotide identity) and AAI (the average amino acid identity) at the genome level of the found strains and the isolated strains were analyzed and verified (Rodriguez-R L. M. & Konstantinidis K. T., PeerJ Preprints 4 :e1900v1 (2016)).

Table 3 below shows the results of analyzing the 16S rRNA gene homology, DDH, ANI and AAI of three standard strains exhibiting the highest homology with the isolated strains in DDH analysis.

TABLE 3

|  | Bacillus amyloliquefaciens plantarum | Bacillus amyloliquefaciens | Bacillus subtilis spizizenii | Criteria for species distinction |
|---|---|---|---|---|
| Standard strains | FZB42 | DSM7 | NRRL B-23049 |  |
| 16S rRNA | 99.67 to 99.73% | 99.46 to 99.66% | 99.18 to 99.39% | 98.65% |
| DDH | 92.10% | 78.60% | 32.70% | 70% |
| ANI | 98.65% | 93.59% | 80.04% | 95% |
| AAI | 98.79% | 95.09% | 79.88% | 95% |

Through the comparison of the whole-length genomes and the 16S rRNA genes as described above, the isolated strain was identified as a microorganism belonging to *Bacillus amyloliquefaciens*. The isolated strain was named *Bacillus amyloliquefaciens* GF423 and deposited with the Korean Collection for Type Culture (KCTC), an international depository authority, on Mar. 6, 2017 under accession number KCTC 13222BP.

The nucleotide database at the National Center for Biotechnology Information was searched, and as a result, an organism having 100% homology to the 16S rRNA genes (SEQ ID NOs: 3 to 11) of the strain of the present invention was not found.

EXAMPLE 2

Isolation/Purification of Superoxide Dismutase (SOD) from *Bacillus Amyloliquefaciens* GF423

2.1: Cultivation of *Bacillus Amyloliquefaciens* GF423

For the cultivation of the *Bacillus amyloliquefaciens* GF423 strain, the single colony formed on the LB agar medium (Luria-Bertani (LB) agar; 10 g/L tryptophan, 5 g/L yeast extract, 10 g/L NaCl, 15 g/L agar) was inoculated in 30 ml of LB medium and cultured in 37° C. for 12 hours. The seed culture was then inoculated in 3 L of LB medium containing 1 mM manganese sulfate ($MnSO_4$) and cultured at 37° C. for 20 hours.

2.2: Isolation and Purification of Superoxide Dismutase

The cell culture was centrifuged at 3,578×g at 4° C. for 20 minutes, and the supernatant was collected and 10-fold concentrated by ultrafiltration (hereinafter referred to as UF; MWCO 10,000). While 300 ml of the concentrated supernatant was stirred at 4° C., ammonium sulfate was added to the supernatant to a saturation degree of 60% and then stirred for 30 minutes. Next, the stirred solution was centrifuged at 3,578 g for 30 minutes, and the supernatant was collected and loaded on HiPrep™ Phenyl HP 16/10 column equilibrated with 50 mM potassium phosphate (pH 7.5) containing 2M ammonium sulfate. Next, proteins were eluted with a linear gradient of 2 M to 0 M ammonium sulfate equilibrated in 50 mM potassium phosphate buffer (pH 7.5) (FIG. 1A).

The SOD-containing fractions (#35 to #40) were collected, concentrated by UF (MWCO 10,000), and desalted by dialysis with 50 mM potassium phosphate (pH 7.5). The protein concentration was measured using the method described in Bradford M, Anal Biochem, 72, 248-254, 1976). The purification profile is shown in FIG. 1.

The activity of superoxide dismutase was analyzed using a superoxide dismutase analysis kit (Cayman Chemical, Michigan, USA). One unit of superoxide dismutase was defined as the amount of enzyme that inhibited 50% of superoxide radicals. The activity of the purified SOD was 2231.12±269 U/mg, and the molecular of the SDS was about 22,000 Dalton.

EXAMPLE 3

Identification of Superoxide Dismutase (SOD) Gene from *Bacillus Amyloliquefaciens* GF423

The N-terminus of the purified SOD was analyzed using the Edman degradation method, and as a result, an amino acid sequence of Ala-Tyr-Lys-Leu-Pro-Glu was found. Genes capable of encoding the above amino acid sequence were searched for, and as a result, a gene of SEQ ID NO: 1 was found.

In order to verify whether the gene of SEQ ID NO: 1 would be a gene encoding the SOD, the gene of SEQ ID NO: 1 was inactivated as shown in FIG. 2. As an erythromycin-resistance gene, a 1144-bp PCR amplification was obtained from a pDG1664 plasmid (Guerout-Fleury, A. M. et al., Gene 180:57-61 (1996)) by use of oligo primers, EmF (gaagcaaacttaagagtgtg) and EmR (tccttggaagctgtcagtag). As DNA fragments homologous to both flanking regions of the gene of SEQ ID NO: 1, a 778-bp PCR product was obtained by amplification using the genome of *Bacillus amyloliquefaciens* GF423 as a template and a combination of primer 1 (aaacagctg ggatgaacacaagtgagag) and primer 2 (cacactct-taagtttgcttc caattctggaagtttgtaag), and a 796-bp PCR product was obtained by amplification using a combination of primer 3 (ctactgacagcttccaaggatacctgaactaccaaaaccg) and primer 4 (aaacagctg aagctcatgaccacagcaag). The PCR products were ligated with the erythromycin-resistance gene by PCR to obtain a single DNA fragment. The ligated DNA was inserted into the Pvull restriction enzyme site of a pUori-ts-cm plasmid (FIG. 3). The resulting plasmid pUori-sodem (FIG. 3) was transfected into *B. amyloliquefaciens* GF423 by the method of Zhang et al. (Zhang G. Q. et al., Anal Biochem. 409:130-137 (2011)). A transformant was selected in LB medium (containing chloramphenicol (10 µg/ml) and erythromycin (5 µg/ml)) at 30° C., and then inoculated and cultured in LB medium containing erythromycin (5 µg/ml) at 37° C. for 16 hours. The culture was plated on LB agar medium containing erythromycin (5 µg/ml) and incubated at 37° C. to form colonies, and colonies having sensitivity to chloramphenicol were selected from the formed colonies, thereby obtaining a strain in which the SOD gene was inactivated.

The SOD activity of the strain in which the gene of SEQ ID NO: 1 was inactivated was compared with that of the parent strain, and as a result, it was seen that the SOD activity of the inactivated strain (3.1 SOD U/ml) was at least 10 times lower than that of the parent strain (41.4 SOD U/ml) at the same cell concentration ($OD_{600}$). This indicates that the gene of SEQ ID NO: 1 encodes a major polypeptide having SOD activity, which is produced by *Bacillus amyloliquefaciens* GF423.

EXAMPLE 4

Comparison of Identity of *Bacillus Amyloliquefaciens* SOD to Melon SOD

Examination was performed of the amino acid sequence identity of the SOD, produced by the *Bacillus amylolique-* faciens GF423 strain, to the amino acid sequences of SODs present in *Cucumis* melon mitochondria (XP_008457298, XP_008457297) chloroplasts (XP_008453838, XP_008450700, XP_008450699, XP_008465422, NP_001315382), and cytosols (XP_008441989, XP_008455578, XP_008455574, ALO62043, ALO62042), and as a result, all the melon SODs exhibited an identity of 40% or less. Table 4 below shows identity and similarity.

TABLE 4

|  | Melon mitochondria SOD X1 | Melon mitochondria SOD X2 |
|---|---|---|
| *Bacillus amyloliquefaciens* GF423 SOD | 36.2% (51.0%) | 30.7% (43.2%) |

FIG. 4 shows the results of analyzing the identity of the SOD, produced by the *Bacillus amyloliquefaciens* GF423 strain of the present invention, to melon mitochondria SOD.

EXAMPLE 5

Production of Superoxide Dismutase (SOD) from *Bacillus Amyloliquefaciens* Gf423

5.1: Culturing of *Bacillus Amyloliquefaciens* GF423

For the cultivation of the strain, the single colony formed on the LB agar medium was inoculated in 50 ml of LB medium and cultured at 37° C. for 12 hours. The seed culture was then inoculated in 500 ml of LB medium and cultured at 37° C. for 6 hours. The second seed culture was then inoculated in 50 L of LB medium containing 1 mM manganese sulfate and cultured at 37° C. for 20 hours. FIG. 5 shows the cultivation profile of *Bacillus amyloliquefaciens* GF423.

5.2: Process after Cultivation of *Bacillus Amyloliquefaciens* GF423

0.7% dipotassium hydrogen phosphate ($K_2HPO_4$) was added to the cell culture, and 1.4% calcium chloride ($CaCl_2$)) was added to the mixture. Next, 0.7% dipotassium hydrogen phosphate was added again, and the mixture was stirred for 30 minutes to induce flocculation. Then, the mixture was centrifuged at 3,578 g at 4° C., and the supernatant was collected and 10-fold concentrated by UF (MWCO 10,000).

5.3: Coating of Superoxide Dismutase

The superoxide dismutase from *Bacillus amyloliquefaciens* GF423 was coated with the natural coating agent shellac. Shellac was dissolved in 50 mM potassium phosphate (pH 7.0) buffer and mixed with the purified superoxide dismutase solution, and the mixture was freeze-dried. The freeze-dried sample was stored in a powder state at 4° C.

Table 5 shows coating efficiency at varying shellac concentrations.

TABLE 5

| Wt % of shellac relative to dry weight of SOD (w/w) | SOD activity measured immediately after suspension of coated SOD in buffer | SOD activity measured at 24 hours after suspension | Coating efficiency (%)* |
|---|---|---|---|
| 0.6 | 22.2 | 655.3 | 96.6 |
| 1.2 | 22.1 | 666.2 | 96.7 |
| 2.3 | 17.6 | 648.1 | 97.3 |
| 3.5 | 15.4 | 618.1 | 97.5 |
| 3.9 | 13.9 | 653.6 | 97.9 |

*(1-(SOD activity measured immediately after suspension of coated SOD in buffer/SOD titer measured at 24 hours after suspension))*100

EXAMPLE 6

Measurement of Activity of Superoxide Dismutase (SOD)

The activity of the purified superoxide dismutase from the *Bacillus amyloliquefaciens* GF423 strain was measured using an SOD activity assay kit (cayman 706002).

First, each of a standard sample and SOD samples were prepared by dilution in 50 mM Tris-HCl (pH 8.0), and 200 µl of a radical detector was dispensed into each well of a 96-well plate, after which 10 µl of each of the standard sample and the SOD samples was dispensed into each well. Next, 20 µl of xanthine oxidase was dispensed into each well, and each well was incubated at room temperature for 30 minutes, after which the absorbance at 450 nm was measured. From the absorbance values of the standard samples, linearized rate (LR) values were calculated to prepare a standard curve. Using an equation obtained from the standard curve, the activity of the superoxide dismutase was calculated by the following equation 1:

$$\text{SOD activity (U/ml)} = [\{(LR - y\text{-intercept})/\text{slope}\} * 23]$$
*dilution factor     Equation 1

For example, linearized rate of standard sample A (Std A LR)=O.D. of standard sample A/O.D. of standard sample A.

Linearized rate of standard sample B (Std A LR)=O.D. of standard sample A/O.D. of standard sample B.

The activity of the superoxide dismutase (GF423 SOD) produced by the *Bacillus amyloliquefaciens* GF423 strain of the present invention was compared with the SOD activities of other products. For comparison, the activity of GF423 SOD produced by the strain of the present invention was compared with those of *Opunitia humifusa* SOD (Xi'an Hao-Xuan Bio-Tech Co., Ltd.), plant herb SOD (Xi'an Hao-Xuan Bio-Tech Co., Ltd.) and melon SOD (BioNov). The results are shown in Table 6 below:

TABLE 6

|  | SOD | Active concentration (unit/ml) |
|---|---|---|
| Example 1 | B. a GF423 SOD | 1413.1 |
| Comparative Example 1 | Hao Xuan Opunitia humifusa SOD | 99.24 |
| Comparative Example 2 | Plant herb SOD | 10.34 |
| Comparative Example 3 | BioNov melon SOD | 93.6 |

EXAMPLE 7

Antioxidant Effect of SOD Produced by *Bacillus Amyloliquefaciens* GF423 Strain In order to evaluate the antioxidant and anti-inflammatory effects of the SOD from the *Bacillus amyloliquefaciens* GF423 strain in animal models, a test was conducted.

The animal test was performed in accordance with the Animal Use and Care Protocol of the Institutional Animal Care and Use Committee (IACUC). As test animals, 7-week-old male SD experimental mice were purchased, were acclimated for one week, divided into four groups as follows, and were housed in an environment at 24° C. and 55±10% humidity with a 12-hr light/12-hr dark cycle.

The animal test was performed on the following four divided groups, each consisting of 7 animals: a control group (group I); a group administered with the SOD produced by the *Bacillus amyloliquefaciens* GF423 strain (group II); a group irradiated with gamma rays to induce stress-induced inflammatory responses (group III); and a group administered with the SOD (produced by the *Bacillus amyloliquefaciens* GF423 strain) after gamma-ray irradiation (group IV). To group I, 100 µl of PBS was administered orally every day, and to group II, 10 units/100 µl of the SOD produced by the *Bacillus amyloliquefaciens* GF423 strain was administered orally every day. To group III, 2 Gy of gamma rays were irradiated on days 0, 6, 13, 20 and 27 in order to induce stress, and 100 µl of PBS was administered orally every day. Group IV was irradiated with gamma-rays in the same manner as group III and was orally administered every day with 10 units/100 µl of the SOD produced by the *Bacillus amyloliquefaciens* GF423 strain.

After the administration, the weight change was measured every day, and blood samples were taken on days 0, 7, 14, 21 and 28. The taken blood samples were incubated at room temperature for 30 minutes, and were then centrifuged at 13,000 rpm for 30 minutes to obtain serum.

1) Measurement of Weight Change of Mice

During the animal test, the weight change of the mice was measured and recorded every day, and the results are shown in FIG. 7. As shown in FIG. 7, the control group (group I) exhibited the greatest weight gain compared to other groups, and the weight gains of other groups were smaller than that of the control group due to the effect of SOD or gamma-rays.

2) Measurement of Change of Antioxidant Enzymes in Blood

Measurement of SOD Activity Change

Using the serum obtained after the animal test, blood SOD activity was measured, and the results are shown in FIG. 8. Referring to FIG. 8, it was seen that the blood SOD activity in group II (administered with the SOD produced by the GF423 strain) increased compared to that in the control group and that the SOD activity in group III (irradiated with gamma rays) decreased. It was seen that the blood SOD activity in group IV (administered with the SOD produced by the GF423 strain), which was irradiated with gamma-rays and administered with the strain of the present invention, was higher than that in group III irradiated with only gamma-rays and was similar to that in the control group (group I).

Measurement of Catalase (CAT) Change

Using the serum obtained after the animal test, blood CAT activity was measured using a catalase assay kit (cayman 707002).

Each of catalase control and serum samples were prepared by dilution in catalase sample buffer (25 mM $KH_2PO_4$, pH 7.5, 1 mM EDTA, 0.1% BSA), and 100 µl of catalase assay buffer (100 mM $KH_2PO_4$, pH 7.0) was dispensed into each well of a 96-well plate, and 30 µl of methanol was dispensed into each well. Next, 20 µl of each of the catalase control and standard samples was dispensed into each well. Then, 20µl of hydrogen peroxide was dispensed into well which was then incubated at room temperature for 20 minutes. Next, 30 µl of potassium hydroxide was dispensed into each well and 30 µl of catalase purpald was added to each well, followed by incubation at room temperature for 10 minutes.

Finally, 10 µl of potassium periodate was added to each well which was then incubated for 5 minutes, and the absorbance at 540 nm was measured. Using the values obtained by subtracting the absorbance value of the standard sample (concentration: 0) from the absorbance values of the standard sample and the serum samples, a standard curve was prepared. Using the equation obtained from the standard curve, the formaldehyde concentration of the serum sample was calculated. Using the concentration value, catalase activity was calculated, and the results are graphically shown in FIG. 9.

Formaldehyde concentration (uM)=[(sample O.D.−$y$ intercept)/slope]*(0.17 ml/0.02 ml)    Equation 2

CAT activity (nmol/min/ml)=(formaldehyde concentration of sample/20 min)*dilution factor Referring to the results in FIG. 9, it was seen that there was no significant change in the catalase activity of the control group and that the catalase activity on day 28 was higher in group II (administered with the SOD produced by the GF423 strain) than in the control group. In addition, it could be seen that the catalase activity in group III (irradiated with gamma rays) decreased and that the rate of catalase in group IV (gamma-ray irradiation+GF423 strain-produced SOD) was reduced by gamma-ray irradiation and then restored to the level of the control group by the administration of the SOD produced by the GF423 strain.

Measurement of Glutathione Peroxidase (GPx) Change

Using the serum obtained after the animal test, blood GPx activity was measured using a glutathione peroxidase assay kit (cayman 703102), and the results are shown in FIG. 10.

First, glutathione peroxidase (control) and serum samples were prepared by dilution in sample buffer (50 mM Tris-HCl, pH 7.6, 5 mM EDTA, 1 mg/ml BSA). To the background well of a 96-well plate, 120 µl of assay buffer (50 mM Tris-HCl, pH 7.6, 5 mM EDTA) and 50 µl of a co-substrate mixture (NADPH, glutathione, glutathione reductase) were added, and to a positive control well and serum sample wells, 100 µl of the assay buffer and 50 µl of the co-substrate mixture were added, and then 20 µl of each of the control and serum samples was dispensed to each well. Next, 20 µl of cumene hydroperoxide was added to each well and well stirred for several seconds, and then the absorbance at 340 nm was measured 5 times or more for 1 minute each time. Based on the time-dependent absorbance, $\Delta A 340$/min was calculated. Based on the $\Delta A 340$/min value, glutathione peroxidase activity was calculated using the following equation 3, and the results are graphically shown in FIG. 10.

$\Delta A$ 340/min=|$A$340(time 2)O.D.−$A$340(time 1)O.D.|/ {Time 2 (min)−Time 1 (min)}    Equation 10

GPx activity (nmol/min/ml)=($\Delta A$ 340/min/0.00373 $uM^{-1}$)*(0.19 ml/0.02 ml)*dilution factor Referring to FIG. 10, it was seen that the change of glutathione peroxidase activity in the control group was not significant and the glutathione peroxidase activity in group II (administered with the SOD produced by the GF423 strain) increased compared to that in the control group (group I). In addition, it was seen that the GPx activity in group III (irradiated with gamma rays) decreased and the GPx activity in group IV (gamma-ray irradiation+GF423 strain) was reduced by gamma-ray irradiation and then restored to the original level by administration of the SOD produced by the GF423 strain of the present invention.

EXAMPLE 8

Verification of Anti-Inflammatory Effect of *Bacillus Amyloliquefaciens* GF423 Strain 1) Measurement of Change in Blood IL-1β (Interleukin-1 Beta)

Using the serum obtained after the animal test, changes in blood IL-1β concentration were measured using an IL-1β ELISA assay kit (mouse IL-1β immunoassay kit, R&D system SMLB00C).

First, a mouse IL-1β control was dissolved in distilled water, and an IL-1β standard sample and serum samples were prepared by dilution in calibrator diluent RD5-16. To each well of a plate coated with mouse IL-1β monoclonal antibody, 50 µl of assay diluent RD1N was added, and then 50 µl of each of the prepared control, standard sample and serum samples was dispensed, followed by incubation at room temperature for 2 hours. Next, each well was washed five times with washing buffer (1× PBS, 0.1% tween-20), and 100 µl of a mouse IL-1β conjugate (horseradish peroxidase-conjugated mouse IL-1β polyclonal antibody) was dispensed into each well, followed by incubation at room temperature for 2 hours. Next, each well was washed five times, and 100 µl of a mixture of color development reagents A (hydrogen peroxide) and B (tetramethylbenzidine) mixed in the same amounts (premixed at 15 minutes before use) was dispensed into each well, followed by incubation at room temperature for 30 minutes under a light-shielded condition. Next, 100 µl of a stop solution was added to each well to stop the reaction, and the absorbances at 450 nm and 540 nm were measured. To obtain the concentration of IL-1β, the absorbance value at 450 was subtracted from the absorbance value at 540 nm. Next, the zero-point absorbance value of the standard sample was subtracted from the values of the standard sample, the control and the serum sample, and based on the obtained values, a standard curve was prepared. Using the equation obtained through the standard curve, IL-1β concentration was calculated by the following equation 4, and the results are graphically shown in FIG. 11.

Equation 4

$\Delta O.D. = 540 \text{ nm } O.D. - 450 \text{ nm } O.D.$     1)

$\Delta\Delta O.D. = \Delta O.D. - \text{Std } 0 \Delta O.D.$     2)

IL-1β(pg/ml)={($\Delta\Delta O.D. - y$-intercept)/slope}*dilution factor     3)

Referring to FIG. 11, it was seen that the change in the IL-1β concentration was not significant in the control group (group I) and group II administered with the strain of the present invention and that the IL-1β concentration greatly increased in group III (irradiated with gamma rays). In contrast, an increase in the IL-1β concentration appeared in group IV (gamma-ray irradiation+SOD produced by GF423 strain), but this increase was smaller than that in the group irradiated with only gamma rays.

2) Measurement of TNF-α (Tumor Necrosis Factor-Alpha) Change

Using the serum obtained after the animal test, changes in blood TNF-α concentration were measured using a TNF-α ELISA assay kit (mouse TNF-α immunoassay kit, R&D system SMTA00B).

First, a mouse TNF-α control was dissolved in distilled water, and an TNF-α standard sample and serum samples were prepared by dilution in calibrator diluent RD6-12. To each well of a plate coated with mouse TNF-α monoclonal antibody, 50 µl of assay diluent RD1-63 was added, and then 50 µl of each of the prepared control, standard sample and serum samples was dispensed, followed by incubation at room temperature for 2 hours. Next, each well was washed five times with washing buffer (1× PBS, 0.1% tween-20), and 100 µl of a mouse TNF-α conjugate (horseradish peroxidase-conjugated mouse TNF-α polyclonal antibody) was dispensed into each well, followed by incubation at room temperature for 2 hours. Next, each well was washed five times, and 100 µl of a mixture of color development reagents A (hydrogen peroxide) and B (tetramethylbenzidine) mixed in the same amounts (premixed at 15 minutes before use) was dispensed into each well, followed by incubation at room temperature for 30 minutes under a light-shielded condition. Next, 100 µl of a stop solution was added to each well to stop the reaction, and the absorbances at 450 nm and 540 nm were measured, and the results are graphically shown in FIG. 12.

Referring to FIG. 12, it was seen that the TNF-α concentration in the control group and group II administered with the strain of the present invention did not significantly change and that the TNF-α concentration in group III (irradiated with gamma rays) increased. In contrast, it could be seen that the TNF-α concentration in group IV (gamma-ray irradiation+SOD produced by GF423 strain) was increased by gamma-ray irradiation and then reduced by administration of the SOD produced by the GF423 strain.

3) Measurement of IL-6 Change

Using the serum obtained after the animal test, changes in blood IL-6 concentration were measured using a IL-6 ELISA assay kit (R&D system SM6000B).

First, a mouse IL-6 control was dissolved in distilled water, and an IL-6 standard sample and serum samples were prepared by dilution in calibrator diluent RDST. To each well of a plate coated with mouse IL-6 monoclonal antibody, 50 µl of assay diluent RD1-14 was added, and then 50 µl of each of the prepared control, standard sample and serum samples was dispensed, followed by incubation at room temperature for 2 hours. Next, each well was washed five times with washing buffer (1× PBS, 0.1% tween-20), and 100 µl of a mouse IL-6 conjugate (horseradish peroxidase-conjugated mouse IL-6 polyclonal antibody) was dispensed into each well, followed by incubation at room temperature for 2 hours. Next, each well was washed five times, and 100 µl of a mixture of color development reagents A (hydrogen peroxide) and B (tetramethylbenzidine) mixed in the same amount (premixed at 15 minutes before use) was dispensed into each well, followed by incubation at room temperature for 30 minutes under a light-shielded condition. Next, 100 μl of a stop solution was added to each well to stop the reaction, and the absorbances at 450 nm and 540 nm were measured, and the results are shown in FIG. 13.

Referring to FIG. 13, it was seen that the IL-6 concentration in the control group (group I) and the group administered with the strain of the present invention did not significantly change and that the IL-6 concentration in group III (irradiated with gamma rays) increased. On the other hand, the IL-6 concentration change in group IV (gamma-ray irradiation+SOD produced by GF423 strain) was similar to that in the group administered with GF423 SOD alone.

4) Measurement of Nitric Oxide (NO) Change

Using the serum obtained after the animal test, changes in blood nitric oxide concentration were measured using an in vitro nitric oxide assay kit (cell biolabs STA-802).

A sodium nitrate standard sample (14 mM) was prepared by dilution in distilled water, and serum samples were prepared by dilution in PBS. 50μ of each of the diluted standard sample and serum samples was dispensed into each well of a 96-well plate, and 50 μl of an enzyme reaction mixture prepared by mixing nitric reductase and enzyme cofactor (sodium hydroxide) was dispensed into each well. Next each well was incubated at room temperature for 1 hour under a light-shielded condition, and 50 μl of Griess reagent A and 50 μl of Griess reagent B were sequentially dispensed, after which each well was incubated at room temperature for 10 minutes so as to induce color development, and the absorbance at 540 nm was measured. Using the absorbance of the standard sample, a standard curve was prepared. Using the equation obtained through the standard curve, the nitric oxide concentration was calculated according to the following equation, and the results are graphically shown in FIG. 14.

$$\text{Nitric nitrogen (NO) concentration (uM)} = \{(\text{sample O.D.} - y\text{-intercept})/\text{slope}\} * \text{dilution factor} \quad \text{Equation 5}$$

Referring to FIG. 14, it was seen that the nitric oxide concentration in the control group and group II administered with the strain of the present invention did not significantly change and that the nitric oxide concentration in group III (irradiated with gamma rays) increased. On the other hand, it was seen that the nitric oxide concentration in group IV (gamma-ray irradiation+SOD produced by GF423 strain) was increased by gamma-ray irradiation and then reduced to the original level by administration of the SOD produced by the GF423 strain.

EXAMPLE 9

Effect of SOD Purified from *Bacillus amyloliquefaciens* GF423 on Inhibition of Colorectal Cancer Cell Proliferation According to the method described below, the degree of inhibition of colorectal cancer cells when treated with the SOD produced by the *Bacillus amyloliquefaciens* GF423 strain of the present invention was examined.

Colorectal cancer HT-29 and SW480 cells were seeded into each well of a 96-well plate at a density of $1 \times 10^4$ cells/well and cultured in a 5% $CO_2$ incubator at 37° C. for 24 hours. After 24 hours, the cells were treated with varying concentrations (0, 10, 25, 50, 100, 200, 400 and 800U/ml) of each of the SOD produced by *Bacillus amyloliquefaciens* GF423 and commercialized superoxide dismutases (*Opunitia humifusa* SOD (Xi'an Hao-Xuan Bio-Tech Co., Ltd.), plant herb SOD (Xi'an Hao-Xuan Bio-Tech Co., Ltd.) and melon SOD (BioNov)) and incubated in a 5% $CO_2$ incubator at 37° C. for 48 hours. Next, 10 μl of a WST-8 (WST-8 cell proliferation kit, Cayman 10010199) mixture was dispensed into each well, and then each well was incubated in a 5% $CO_2$ incubator at 37° C. for 1 hour, and then the absorbance at 450 nm was measured. The measured absorbance value was compared with the absorbance value of the control group, and the percent inhibition of proliferation of the cells was calculated according to the following equation 6, and the results are shown in FIGS. 6A and 6B.

$$\text{Cell proliferation (\%)} = (\text{O.D. at each concentration}/\text{control O.D.}) * 100 \quad \text{Equation 6}$$

Referring to FIG. 6A, it can be seen that the effect of the SOD, produced by the strain of the present invention, on the inhibition of cell proliferation was better than those of commercialized *Opunitia humifusa* SOD, plant herb SOD and melon SOD. In particular, the difference in the effect was remarkable at low concentrations (10 U/ml and 25 U/ml). Namely, at an SOD concentration of 10 U/ml, *Opunitia humifusa* SOD and melon SOD had no inhibitory effect on the proliferation of colorectal cancer SW480 cells, whereas plant herb SOD and GF423 SOD showed an inhibitory effect of about 10%. At an SOD concentration of 25 U/ml, plant herb SOD showed an inhibitory effect of about 10%, and the GF423 SOD of the present invention showed an high inhibitory effect of about 40%.

Referring to FIG. 6B, *Opunitia humifusa* SOD, plant herb SOD and melon SOD (BioNov) showed a low inhibitory effect (about 10% or less) on the proliferation of colorectal cancer HT 29 cells up to an SOD concentration up to 100 U/ml, whereas the GF423 SOD of the present invention started to show the inhibitory effect from a concentration of 25 U/ml and showed an inhibitory effect of about 15% at 25 U/ml, an inhibitory effect of 30% at 50 U/ml, and a very excellent inhibitory effect (50%) on the proliferation of colorectal cancer cells at a concentration of 100 U/ml.

As can be seen from these results, the polypeptide having SOD activity, produced by the *Bacillus amyloliquefaciens* GF423 strain of the present invention, showed an inhibitory effect on the proliferation of colorectal cancer cells and also showed excellent inhibitory effects at lower concentrations compared to commercialized SODs.

EXAMPLE 10

Anti-Hyperlipidemic Effect of SOD from *Bacillus Amyloliquefaciens* GF423 Strain In this Example, an experiment was performed to examine the effects of the superoxide dismutase (SOD) from the *Bacillus amyloliquefaciens* GF423 strain on lipid metabolisms in hyperlipidemic patients and normal persons.

In order to demonstrate the preventive and therapeutic effects of the composition of the present invention against hyperlipidemia, the superoxide dismutase having the amino acid sequence of SEQ ID NO: 2 was administered to 22 normal persons (normal group) and 44 hyperlipidemic patients (risk group) for a predetermined period of time, and then blood total cholesterol (TC), triglyceride (TG), LDL cholesterol and HDL cholesterol concentrations were measured.

In this Example, according to the composition shown in Table 7 below, the superoxide dismutase having the amino acid sequence of SEQ ID NO: 2 was mixed with excipients such that each capsule contained 250 U of the superoxide dismutase. The composition of the present invention, prepared in this manner, was administered orally to each subject of the two groups once a day (one capsule per day; 250 Unit/day).

TABLE 7

| Component | Content (wt %) |
|---|---|
| SOD enzyme (15 µg/mg) | 3.70% |
| Mannitol | 69.49% |
| Vanilla fragrance powder | 0.44% |
| Strawberry flavor powder | 8.79% |
| Peach concentrate powder | 17.58% |
| 250 U/capsule | 100.00% |

Efficacy Evaluation Method—Lipid Parameters

4 Weeks before and after administration of the superoxide dismutase of the present invention, the HDL-cholesterol, LDL-cholesterol, total cholesterol and triglyceride concentrations in whole blood were measured. The total cholesterol concentration in the blood obtained from each subject in the above-described Experimental Example was measured with an assay reagent (Asan Pharmaceutical kit) by use of the method of Allain et al. (Clin. Chem. 20: 470-475, 1974). HDL-cholesterol concentrations were measured using Asan Pharmaceutical reagent (Clin. Chem. 28: 1379-1388, 1982). Blood triglyceride (TG) concentrations were measured colorimetrically using triglyceride assay reagent (Asan Pharmaceutical kit) according to the method of McGowan et al. (Clin. Chem. 29: 538-542, 1983). The results of the measurement are shown in Table 8 below. All values were expressed as mean±standard deviation (SD). For the pharmaceutical composition of the present invention, no side effect was observed in all the subjects.

As shown in Table 8 above, the placebo group showed no significant changes in the total cholesterol, triglyceride and low-density cholesterol concentrations even when there were slight changes in the concentrations. In contrast, in the hyperlipidemic patient group administered with the pharmaceutical composition which contained the superoxide dismutase of the present invention as an active ingredient, the total cholesterol, triglyceride, and low-density cholesterol concentrations were significantly lowered compared to those before the administration.

Although the present invention has been described in detail above, the description is intended merely to illustrate specific implementations of the present invention, and the scope of the present invention is not limited by the description. It will be apparent to a person having ordinary knowledge in the art to which the present invention pertains that various modifications and/or alterations may be made without departing from the spirit and scope of the present invention. Therefore, the substantial range of protection of the present invention should be defined based on the attached claims and equivalents thereto.

INDUSTRIAL APPLICABILITY

The polypeptide having superoxide dismutase (SOD) activity according to the present invention has excellent antioxidant, anti-inflammatory and anticancer activities, an excellent activity of preventing or treating hyperlipidemia, excellent stability of enzymatic activity, and excellent in vivo stability. Accordingly, it can be advantageously used as a material for foods, health supplement foods, pharmaceutical drugs, cosmetic drugs, and the like, which contain SOD.

SEQUENCE LISTING FREE TEXT

SEQ ID NO: 1 is the nucleotide sequence of a gene encoding a superoxide dismutase produced by a *Bacillus amyloliquefaciens* GF423 strain.

SEQ ID NO: 2 is the amino acid sequence of a superoxide dismutase produced by a *Bacillus amyloliquefaciens* GF423 strain.

SEQ ID NOs: 3 to 11 are the nucleotide sequences of the 16s rRNA genes of a *Bacillus amyloliquefaciens* GF423 strain.

TABLE 8

| Group | | Placebo group | | Group administered with SOD | |
|---|---|---|---|---|---|
| | | Normal group | Patient group | Normal group | Patient group |
| Total cholesterol (mmol/L) | 0 day | 171.2 ± 21.7 | 230 ± 30.4 | 175.9 ± 22.62 | 224.4 ± 21.17 |
| | After 4 weeks | 173.5 ± 25.3 | 231 ± 18.9 | 163.3 ± 17.80 | 198.8 ± 12.40* |
| Triglyceride (TG) (mmol/L) | 0 day | 93.6 ± 17.3 | 160.1 ± 22.4 | 96.41 ± 28.39 | 237.36 ± 138.94 |
| | After 4 weeks | 93.5 ± 15.5 | 159.8 ± 23.7 | 90.75 ± 27.52 | 161.75 ± 77.24 |
| HDL-C (mmol/L) | 0 day | 56.2 ± 13.2 | 32 ± 11.3 | 56.16 ± 12.21 | 35 ± 0 |
| | After 4 weeks | 54.3 ± 13.4 | 33 ± 12.7 | 55 ± 13.36 | 35 ± 0 |
| LDL-C (mmol/L) | 0 day | 100.5 ± 14.2 | 166.5 ± 20.4 | 94.74 ± 17.60 | 151.17 ± 22.25 |
| | After 4 weeks | 102.6 ± 15.8 | 166.8 ± 21.7 | 92.38 ± 16.28 | 123.34 ± 19.20* |

The invention claimed is:

1. A method for producing a pharmaceutical composition comprising a polypeptide having superoxide dismutase activity and comprising SEQ ID NO:2, for preventing or treating cancer or hyperlipidemia, the method comprising:

formulating the polypeptide having superoxide dismutase activity isolated from a culture obtained by culturing a *Bacillus amyloliquefaciens* GF423 strain, KCTC 13222BP, with an excipient or a carrier.

2. A method for treating hyperlipidemia in a subject, comprising:

administering to the subject in need of such treatment a pharmaceutical composition comprising a pharmaceutically effective amount of a superoxide dismutase produced by a *Bacillus amyloliquefaciens* GF423 strain, KCTC 13222BP, and an excipient or a carrier, wherein the superoxide dismutase comprises the amino acid sequence of SEQ ID NO: 2.

* * * * *

SEQUENCE LISTING

<160> NUMBER OF SEQ ID NOS: 11

<210> SEQ ID NO 1
<211> LENGTH: 606
<212> TYPE: DNA
<213> ORGANISM: Bacillus amyloliquefaciens

<400> SEQUENCE: 1

```
atggcttaca aacttccaga attgccttac gcttatgatg ctttagaacc tcatatcgat      60
aaggaaacga tgacgattca ccatacgaag caccataaca catacgtgac aaacctcaac     120
aaagcgatcg aaggatctgc gcttgcagag aaatctgtag atgagcttgt tgctgatttg     180
aacgcagtgc cggaggacat ccgcacggca gtccgcaaca atggcggcgg acatgcaaac     240
cactctttat tctggactct tttatctccg aacggcggag gcgaaccgac tggtgagctt     300
gctgaagaga tcaaaagcac gttcggaagc ttcgatcaat ttaaagaaaa attcgccgca     360
gcagctgcag gccgtttcgg ttcaggctgg gcttggctcg ttgtaaacaa cggcaaactt     420
gaaattacaa gcacgccaaa ccaagattca ccgctttcag aaggtaaaac acctgttctc     480
ggtcttgatg tttgggagca tgcgtactac ctgaactacc aaaaccgccg tcctgattac     540
atttcagctt tctggaatgt tgtgaactgg gatgaagttg cccgtcttta cagcgaagca     600
aaataa                                                               606
```

<210> SEQ ID NO 2
<211> LENGTH: 201
<212> TYPE: PRT
<213> ORGANISM: Bacillus amyloliquefaciens

<400> SEQUENCE: 2

```
Met Ala Tyr Lys Leu Pro Glu Leu Pro Tyr Ala Tyr Asp Ala Leu Glu
1               5                   10                  15

Pro His Ile Asp Lys Glu Thr Met Thr Ile His Thr Lys His His
            20                  25                  30

Asn Thr Tyr Val Thr Asn Leu Asn Lys Ala Ile Glu Gly Ser Ala Leu
        35                  40                  45

Ala Glu Lys Ser Val Asp Glu Leu Val Ala Asp Leu Asn Ala Val Pro
    50                  55                  60

Glu Asp Ile Arg Thr Ala Val Arg Asn Asn Gly Gly His Ala Asn
65                  70                  75                  80

His Ser Leu Phe Trp Thr Leu Leu Ser Pro Asn Gly Gly Glu Pro
                85                  90                  95

Thr Gly Glu Leu Ala Glu Glu Ile Lys Ser Thr Phe Gly Ser Phe Asp
            100                 105                 110

Gln Phe Lys Glu Lys Phe Ala Ala Ala Ala Ala Gly Arg Phe Gly Ser
        115                 120                 125

Gly Trp Ala Trp Leu Val Val Asn Asn Gly Lys Leu Glu Ile Thr Ser
    130                 135                 140

Thr Pro Asn Gln Asp Ser Pro Leu Ser Glu Gly Lys Thr Pro Val Leu
145                 150                 155                 160

Gly Leu Asp Val Trp Glu His Ala Tyr Tyr Leu Asn Tyr Gln Asn Arg
                165                 170                 175

Arg Pro Asp Tyr Ile Ser Ala Phe Trp Asn Val Val Asn Trp Asp Glu
            180                 185                 190

Val Ala Arg Leu Tyr Ser Glu Ala Lys
        195                 200
```

```
<210> SEQ ID NO 3
<211> LENGTH: 1543
<212> TYPE: DNA
<213> ORGANISM: Bacillus amyloliquefaciens

<400> SEQUENCE: 3
agagtttgat cctggctcag gacgaacgct ggcggcgtgc ctaatacatg caagtcgagc      60
ggacagatgg gagcttgctc cctgatgtca gcggcggacg ggtgagtaac acgtgggtaa     120
cctgcctgta agactgggat aactccggga aaccggggct aataccggat ggttgtttga     180
accgcatggt tcagacataa aaggtggctt cggctaccac ttacagatgg acccgcggcg     240
cattagctag ttggtgaggt aacggctcac caaggcaacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
gacggtacct aaccagaaag ccacggctaa ctacgtgcca gcagccgcgg taatacgtag     540
gtggcaagcg ttgtccggaa ttattgggcg taaagggctc gcaggcggtt tcttaagtct     600
gatgtgaaag cccccggctc aacccgggag ggtcattgga aactgggaa cttgagtgca     660 gaagaggaga gtggaattcc acgtgtagcg gtgaaatgcg tagagatgtg gaggaacacc     720
agtggcgaag gcgactctct ggtctgtaac tgacgctgag gagcgaaagc gtggggagcg     780
aacaggatta gataccctgg tagtccacgc cgtaaacgat gagtgctaag tgttagggg     840 tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagagatag    1020
gacgtcccct cggggcag agtgacaggt ggtgcatggt tgtcgtcagc tcgtgtcgtg    1080
agatgttggg ttaagtcccg caacgagcgc aacccttgat cttagttgcc agcattcagt    1140
tgggcactct aaggtgactg ccggtgacaa accggaggaa ggtggggatg acgtcaaatc    1200
atcatgcccc ttatgacctg gctacacacg tgctacaat ggacagaaca aagggcagcg    1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct ttatggagcc agccgccgaa ggtgggacag atgattgggg tgaagtcgta    1500
acaaggtagc cgtatcggaa ggtgcggctg atcacctcc ttt                      1543

<210> SEQ ID NO 4
<211> LENGTH: 1543
<212> TYPE: DNA
<213> ORGANISM: Bacillus amyloliquefaciens

<400> SEQUENCE: 4
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aatagcggat ggttgtttga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
```

```
gaatcttccg caatggacga aagtctgacg gagcaacgcc gcgtgagtga tgaaggtttt      420
cggatcgtaa agctctgttg ttagggaaga acaagtgccg ttcaaatagg gcggcacctt      480
gacggtacct aaccagaaag ccacggctaa ctacgtgcca gcagccgcgg taatacgtag      540
gtggcaagcg ttgtccggaa ttattgggcg taaagggctc gcaggcggtt tcttaagtct      600
gatgtgaaag ccccggctc aaccggggag ggtcattgga aactgggaa cttgagtgca       660 gaagaggaga gtggaattcc acgtgtagcg gtgaaatgcg tagagatgtg gaggaacacc     720
agtggcgaag gcgactctct ggtctgtaac tgacgctgag gagcgaaagc gtggggagcg     780
aacaggatta gataccctgg tagtccacgc cgtaaacgat gagtgctaag tgttagggg      840 tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagagatag    1020
gacgtcccct cgggggcag agtgacaggt ggtgcatggt tgtcgtcagc tcgtgtcgtg     1080
agatgttggg ttaagtcccg caacgagcgc aacccttgat cttagttgcc agcattcagt    1140
tgggcactct aaggtgactg ccggtgacaa accggaggaa ggtggggatg acgtcaaatc    1200
atcatgcccc ttatgacctg gctacacac gtgctacaat ggacagaaca aagggcagcg    1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct ttatggagcc agccgccgaa ggtgggacag atgattgggg tgaagtcgta    1500
acaaggtagc cgtatcggaa ggtgcggctg gatcacctcc ttt                      1543

<210> SEQ ID NO 5
<211> LENGTH: 1543
<212> TYPE: DNA
<213> ORGANISM: Bacillus amyloliquefaciens

<400> SEQUENCE: 5
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtctga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
gacggtacct aaccagaaag ccacggctaa ctacgtgcca gcagccgcgg taatacgtag     540
gtggcaagcg ttgtccggaa ttattgggcg taaagggctc gcaggcggtt tcttaagtct     600
gatgtgaaag ccccggctc aaccggggag ggtcattgga aactgggaa cttgagtgca      660 gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttagggg     840 tttccgcccc ttagtgctgc agctaacgca ttaagcactc cgcctgggga gtacggtcgc    900
```

| | |
|---|---|
| aagactgaaa ctcaaaggaa ttgacggggg cccgcacaag cggtggagca tgtggtttaa | 960 |
| ttcgaagcaa cgcgaagaac cttaccaggt cttgacatcc tctgacaatc ctagagatag | 1020 |
| gacgtcccct tcgggggcag agtgacaggt ggtgcatggt tgtcgtcagc tcgtgtcgtg | 1080 |
| agatgttggg ttaagtcccg caacgagcgc aacccttgat cttagttgcc agcattcagt | 1140 |
| tgggcactct aaggtgactg ccggtgacaa accggaggaa ggtggggatg acgtcaaatc | 1200 |
| atcatgcccc ttatgacctg gctacacac gtgctacaat ggacagaaca aagggcagcg | 1260 |
| aaaccgcgag gttaagccaa tcccacaaat ctgttctcag ttcggatcgc agtctgcaac | 1320 |
| tcgactgcgt gaagctggaa tcgctagtaa tcgcggatca gcatgccgcg gtgaatacgt | 1380 |
| tcccgggcct tgtacacacc gcccgtcaca ccacgagagt ttgtaacacc cgaagtcggt | 1440 |
| gaggtaacct ttatggagcc agccgccgaa ggtgggacag atgattgggg tgaagtcgta | 1500 |
| acaaggtagc cgtatcggaa ggtgcggctg gatcacctcc ttt | 1543 |

<210> SEQ ID NO 6
<211> LENGTH: 1543
<212> TYPE: DNA
<213> ORGANISM: Bacillus amyloliquefaciens

<400> SEQUENCE: 6

| | |
|---|---|
| agagtttgat cctggctcag gacgaacgct ggcggcgtgc ctaatacatg caagtcgagc | 60 |
| ggacagatgg gagcttgctc cctgatgtta gcggcggacg ggtgagtaac acgtgggtaa | 120 |
| cctgcctgta agactgggat aactccggga aaccggggct aataccggat ggttgtttga | 180 |
| accgcatggt tcagacataa aaggtggctt cggctaccac ttacagatgg acccgcggcg | 240 |
| cattagctag ttggtgaggt aacggctcac caaggcgacg atgcgtagcc gacctgagag | 300 |
| ggtgatcggc cacactggga ctgagacacg gcccagactc ctacgggagg cagcagtagg | 360 |
| gaatcttccg caatggacga aagtctgacg gagcaacgcc gcgtgagtga tgaaggtttt | 420 |
| cggatcgtaa agctctgttg ttagggaaga acaagtgccg ttcaaatagg gcggcacctt | 480 |
| gacggtacct aaccagaaag ccacggctaa ctacgtgcca gcagccgcgg taatacgtag | 540 |
| gtggcaagcg ttgtccggaa ttattgggcg taaagggctc gcaggcggtt cttaagtct | 600 |
| gatgtgaaag cccccggctc aaccggggag ggtcattgga aactgggaa cttgagtgca | 660 |
| gaagaggaga gtggaattcc acgtgtagcg gtgaaatgcg tagagatgtg gaggaacacc | 720 |
| agtggcgaag gcgactctct ggtctgtaac tgacgctgag gagcgaaagc gtggggagcg | 780 |
| aacaggatta gataccctgg tagtccacgc cgtaaacgat gagtgctaag tgttagggg | 840 |
| tttccgcccc ttagtgctgc agctaacgca ttaagcactc cgcctgggga gtacggtcgc | 900 |
| aagactgaaa ctcaaaggaa ttgacggggg cccgcacaag cggtggagca tgtggtttaa | 960 |
| ttcgaagcaa cgcgaagaac cttaccaggt cttgacatcc tctgacaatc ctagagatag | 1020 |
| gacgtcccct tcgggggcag agtgacaggt ggtgcatggt tgtcgtcagc tcgtgtcgtg | 1080 |
| agatgttggg ttaagtcccg caacgagcgc aacccttgat cttagttgcc agcattcagt | 1140 |
| tgggcactct aaggtgactg ccggtgacaa accggaggaa ggtggggatg acgtcaaatc | 1200 |
| atcatgcccc ttatgacctg gctacacac gtgctacaat ggacagaaca aagggcagcg | 1260 |
| aaaccgcgag gttaagccaa tcccacaaat ctgttctcag ttcggatcgc agtctgcaac | 1320 |
| tcgactgcgt gaagctggaa tcgctagtaa tcgcggatca gcatgccgcg gtgaatacgt | 1380 |
| tcccgggcct tgtacacacc gcccgtcaca ccacgagagt ttgtaacacc cgaagtcggt | 1440 |
| gaggtaacct ttatggagcc agccgccgaa ggtgggacag atgattgggg tgaagtcgta | 1500 |

-continued

```
acaaggtagc cgtatcggaa ggtgcggctg gatcacctcc ttt                1543

<210> SEQ ID NO 7
<211> LENGTH: 1543
<212> TYPE: DNA
<213> ORGANISM: Bacillus amyloliquefaciens

<400> SEQUENCE: 7
agagtttgat cctggctcag gacgaacgct ggcggcgtgc ctaatacatg caagtcgagc    60
ggacagatgg gagcttgctc cctgatgtta gcggcggacg ggtgagtaac acgtgggtaa   120
cctgcctgta agactgggat aactccggga accggggct aataccggat ggttgtctga   180
accgcatggt tcagacataa aaggtggctt cggctaccac ttacagatgg acccgcggcg   240
cattagctag ttggtgaggt aacggctcac caaggcgacg atgcgtagcc gacctgagag   300
ggtgatcggc cacactggga ctgagacacg gcccagactc ctacgggagg cagcagtagg   360
gaatcttccg caatggacga aagtctgacg gagcaacgcc gcgtgagtga tgaaggtttt   420
cggatcgtaa agctctgttg ttagggaaga acaagtgccg ttcaaatagg gcggcacctt   480
gacggtacct aaccagaaag ccacggctaa ctacgtgcca gcagccgcgg taatacgtag   540
gtggcaagcg ttgtccggaa ttattgggcg taaagggctc gcaggcggtt cttaagtct   600 gatgtgaaag cccccggctc aaccggggag ggtcattgga aactgggaa cttgagtgca   660 gaagaggaga gtggaattcc acgtgtagcg gtgaaatgcg tagagatgtg gaggaacacc   720
agtggcgaag cgactctct ggtctgtaac tgacgctgag gagcgaaagc gtggggagcg   780
aacaggatta gataccctgg tagtccacgc cgtaaacgat gagtgctaag tgttaggggg   840
tttccgcccc ttagtgctgc agctaacgca ttaagcactc cgcctgggga gtacggtcgc   900
aagactgaaa ctcaaaggaa ttgacggggg cccgcacaag cggtggagca tgtggtttaa   960
ttcgaagcaa cgcgaagaac cttaccaggt cttgacatcc tctgacaatc ctagagatag  1020
gatgtcccct tcggggcag agtgacaggt ggtgcatggt tgtcgtcagc tcgtgtcgtg  1080
agatgttggg ttaagtcccg caacgagcgc aaccccttgat cttagttgcc agcattcagt  1140
tgggcactct aaggtgactg ccggtgacaa accggaggaa ggtggggatg acgtcaaatc  1200
atcatgcccc ttatgacctg gctacacac gtgctacaat ggacagaaca aagggcagcg  1260
aaaccgcgag gttaagccaa tcccacaaat ctgttctcag ttcggatcgc agtctgcaac  1320
tcgactgcgt gaagctggaa tcgctagtaa tcgcggatca gcatgccgcg gtgaatacgt  1380
tcccgggcct tgtacacacc gcccgtcaca ccacgagagt ttgtaacacc cgaagtcggt  1440 gaggtaaccct ttatggagcc agccgccgaa ggtgggacag atgattgggg tgaagtcgta  1500
acaaggtagc cgtatcggaa ggtgcggctg gatcacctcc ttt                    1543

<210> SEQ ID NO 8
<211> LENGTH: 1543
<212> TYPE: DNA
<213> ORGANISM: Bacillus amyloliquefaciens

<400> SEQUENCE: 8
agagtttgat cctggctcag gacgaacgct ggcggcgtgc ctaatacatg caagtcgagc    60
ggacagatgg gagcttgctc cctgatgtta gcggcggacg ggtgagtaac acgtgggtaa   120
cctgcctgta agactgggat aactccggga accggggct aataccggat ggttgtctga   180
accgcatggt tcagacataa aaggtggctt cggctaccac ttacagatgg acccgcggcg   240
```

```
cattagctag ttggtgaggt aacggctcac caaggcgacg atgcgtagcc gacctgagag      300
ggtgatcggc cacactggga ctgagacacg gcccagactc ctacgggagg cagcagtagg      360
gaatcttccg caatggacga aagtctgacg gagcaacgcc gcgtgagtga tgaaggtttt      420
cggatcgtaa agctctgttg ttagggaaga acaagtgccg ttcaaatagg gcggcacctt      480
gacggtacct aaccagaaag ccacggctaa ctacgtgcca gcagccgcgg taatacgtag      540
gtggcaagcg ttgtccggaa ttattgggcg taaagggctc gcaggcggtt tcttaagtct      600
gatgtgaaag cccccggctc aaccggggag ggtcattgga aactgggaa cttgagtgca      660
gaagaggaga gtggaattcc acgtgtagcg gtgaaatgcg tagagatgtg gaggaacacc      720
agtggcgaag gcgactctct ggtctgtaac tgacgctgag gagcgaaagc gtggggagcg      780
aacaggatta gataccctgg tagtccacgc cgtaaacgat gagtgctaag tgttaggggg      840
tttccgcccc ttagtgctgc agctaacgca ttaagcactc cgcctgggga gtacggtcgc      900
aagactgaaa ctcaaaggaa ttgacggggg cccgcacaag cggtggagca tgtggtttaa      960
ttcgaagcaa cgcgaagaac cttaccaggt cttgacatcc tctgacaatc ctagagatag     1020
gatgtcccct cgggggcag agtgacaggt ggtgcatggt tgtcgtcagc tcgtgtcgtg     1080
agatgttggg ttaagtcccg caacgagcgc aacccttgat cttagttgcc agcattcagt     1140
tgggcactct aaggtgactg ccggtgacaa accggaggaa ggtggggatg acgtcaaatc     1200
atcatgcccc ttatgacctg gctacacac gtgctacaat ggacagaaca aagggcagcg     1260
aaaccgcgag gttaagccaa tcccacaaat ctgttctcag ttcggatcgc agtctgcaac     1320
tcgactgcgt gaagctggaa tcgctagtaa tcgcggatca gcatgccgcg gtgaatacgt     1380
tcccgggcct tgtacacacc gcccgtcaca ccacgagagt ttgtaacacc cgaagtcggt     1440
gaggtaacct ttatggagcc agccgccgaa ggtgggacag atgattgggg tgaagtcgta     1500
acaaggtagc cgtatcggaa ggtgcggctg gatcacctcc ttt                      1543

<210> SEQ ID NO 9
<211> LENGTH: 1543
<212> TYPE: DNA
<213> ORGANISM: Bacillus amyloliquefaciens

<400> SEQUENCE: 9
agagtttgat cctggctcag gacgaacgct ggcggcgtgc ctaatacatg caagtcgagc       60
ggacagatgg gagcttgctc cctgatgtta gcggcggacg ggtgagtaac acgtgggtaa      120
cctgcctgta agactgggat aactccggga aaccggggct ataccggat ggttgtttga      180
accgcatggt tcagacataa aaggtggctt cggctaccac ttacagatgg acccgcggcg      240
cattagctag ttggtgaggt aacggctcac caaggcaacg atgcgtagcc gacctgagag      300
ggtgatcggc cacactggga ctgagacacg gcccagactc ctacgggagg cagcagtagg      360
gaatcttccg caatggacga aagtctgacg gagcaacgcc gcgtgagtga tgaaggtttt      420
cggatcgtaa agctctgttg ttagggaaga acaagtgccg ttcaaatagg gcggcacctt      480
gacggtacct aaccagaaag ccacggctaa ctacgtgcca gcagccgcgg taatacgtag      540
gtggcaagcg ttgtccggaa ttattgggcg taaagggctc gcaggcggtt tcttaagtct      600
gatgtgaaag cccccggctc aaccggggag ggtcattgga aactgggaa cttgagtgca      660
gaagaggaga gtggaattcc acgtgtagcg gtgaaatgcg tagagatgtg gaggaacacc      720
agtggcgaag gcgactctct ggtctgtaac tgacgctgag gagcgaaagc gtggggagcg      780
aacaggatta gataccctgg tagtccacgc cgtaaacgat gagtgctaag tgttaggggg      840
```

-continued

```
tttccgcccc ttagtgctgc agctaacgca ttaagcactc cgcctgggga gtacggtcgc      900
aagactgaaa ctcaaaggaa ttgacggggg cccgcacaag cggtggagca tgtggtttaa      960
ttcgaagcaa cgcgaagaac cttaccaggt cttgacatcc tctgacaatc ctagagatag     1020
gacgtcccct tcgggggcag agtgacaggt ggtgcatggt tgtcgtcagc tcgtgtcgtg     1080
agatgttggg ttaagtcccg caacgagcgc aacccttgat cttagttgcc agcattcagt     1140
tgggcactct aaggtgactg ccggtgacaa accggaggaa ggtggggatg acgtcaaatc     1200
atcatgcccc ttatgacctg gctacacac gtgctacaat ggacagaaca aagggcagcg     1260
aaaccgcgag gttaagccaa tcccacaaat ctgttctcag ttcggatcgc agtctgcaac     1320
tcgactgcgt gaagctggaa tcgctagtaa tcgcggatca gcatgccgcg gtgaatacgt     1380
tcccgggcct tgtacacacc gcccgtcaca ccacgagagt ttgtaacacc cgaagtcggt     1440
gaggtaacct ttatggagcc agccgccgaa ggtgggacag atgattgggg tgaagtcgta     1500
acaaggtagc cgtatcggaa ggtgcggctg gatcacctcc ttt                      1543

<210> SEQ ID NO 10
<211> LENGTH: 1543
<212> TYPE: DNA
<213> ORGANISM: Bacillus amyloliquefaciens

<400> SEQUENCE: 10
agagtttgat cctggctcag gacgaacgct ggcggcgtgc ctaatacatg caagtcgagc       60
ggacagatgg gagcttgctc cctgatgtta gcggcggacg ggtgagtaac acgtgggtaa      120
cctgcctgta agactgggat aactccggga aaccggggct aataccggat ggttgtctga      180
atcgcatggt tcagacataa aaggtggctt ctgctaccac ttacagatgg acccgcggcg      240
cattagctag ttggtgaggt aacggctcac caaggcgacg atgcgtagcc gacctgagag      300
ggtgatcggc cacactggga ctgagacacg gcccagactc ctacgggagg cagcagtagg      360
gaatcttccg caatggacga aagtctgacg gagcaacgcc gcgtgagtga tgaaggtttt      420
cggatcgtaa agctctgttg ttagggaaga acaagtgccg ttcaaatagg gcggcaccTT      480
gacggtacct aaccagaaag ccacggctaa ctacgtgcca gcagccgcgg taatacgtag      540
gtggcaagcg ttgtccggaa ttattgggcg taaagggctc gcaggcggtt cttaagtct      600 gatgtgaaag cccccggctc aaccggggag ggtcattgga aactgggaa cttgagtgca      660 gaagaggaga gtggaattcc acgtgtagcg gtgaaatgcg tagagatgtg gaggaacacc      720
agtggcgaag gcgactctct ggtctgtaac tgacgctgag gagcgaaagc gtggggagcg      780
aacaggatta gataccctgg tagtccacgc cgtaaacgat gagtgctaag tgttaggggg      840
tttccgcccc ttagtgctgc agctaacgca ttaagcactc cgcctgggga gtacggtcgc      900
aagactgaaa ctcaaaggaa ttgacggggg cccgcacaag cggtggagca tgtggtttaa      960
ttcgaagcaa cgcgaagaac cttaccaggt cttgacatcc tctgacaatc ctagagatag     1020
gacgtcccct tcgggggcag agtgacaggt ggtgcatggt tgtcgtcagc tcgtgtcgtg     1080
agatgttggg ttaagtcccg caacgagcgc aacccttgat cttagttgcc agcattcagt     1140
tgggcactct aaggtgactg ccggtgacaa accggaggaa ggtggggatg acgtcaaatc     1200
atcatgcccc ttatgacctg gctacacac gtgctacaat ggacagaaca aagggcagcg     1260
aaaccgcgag gttaagccaa tcccacaaat ctgttctcag ttcggatcgc agtctgcaac     1320
tcgactgcgt gaagctggaa tcgctagtaa tcgcggatca gcatgccgcg gtgaatacgt     1380
```

```
tcccgggcct tgtacacacc gcccgtcaca ccacgagagt ttgtaacacc cgaagtcggt    1440
gaggtaacct tttaggagcc agccgccgaa ggtgggacag atgattgggg tgaagtcgta    1500
acaaggtagc cgtatcggaa ggtgcggctg gatcacctcc ttt                      1543

<210> SEQ ID NO 11
<211> LENGTH: 1543
<212> TYPE: DNA
<213> ORGANISM: Bacillus amyloliquefaciens

<400> SEQUENCE: 11
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa    120
cctgcctgta agactgggat aactccggga accgggggct aataccagat ggttgtctga    180
accgcatggt tcagacataa aaggtggctt cggctaccac ttacagatgg acccgcggcg    240
cattagctag ttggtgaggt aacggctcac caaggcgacg atgcgtagcc gacctgagag    300
ggtgatcggc cacactggga ctgagacacg gcccagactc ctacgggagg cagcagtagg    360
gaatcttccg caatggacga aagtctgacg gagcaacgcc gcgtgagtga tgaaggtttt    420
cggatcgtaa agctctgttg ttagggaaga caagtgccg ttcaaatagg gcggcacctt    480
gacggtacct aaccagaaag ccacggctaa ctacgtgcca gcagccgcgg taatacgtag    540
gtggcaagcg ttgtccggaa ttattgggcg taaagggctc gcaggcggtt cttaagtct    600 gatgtgaaag cccccggctc aaccggggag ggtcattgga aactgggaa cttgagtgca    660 gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttaggggg    840
tttccgcccc ttagtgctgc agctaacgca ttaagcactc cgcctgggga gtacggtcgc    900
aagactgaaa ctcaaaggaa ttgacggggg cccgcacaag cggtggagca tgtggttaa    960 ttcgaagcaa cgcgaagaac cttaccaggt cttgacatcc tctgacaatc ctagagatag    1020
gacgtcccct tcggggcag agtgacaggt ggtgcatggt tgtcgtcagc tcgtgtcgtg    1080
agatgttggg ttaagtcccg caacgagcgc aaccctttgat cttagttgcc agcattcagt    1140
tgggcactct aaggtgactg ccggtgacaa accggaggaa ggtggggatg acgtcaaatc    1200
atcatgcccc ttatgacctg gctacacacg tgctacaat ggacagaaca aagggcagcg    1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct tttaggagcc agccgccgaa ggtgggacag atgattgggg tgaagtcgta    1500
acaaggtagc cgtatcggaa ggtgcggctg gatcacctcc ttt                      1543
```